(12) United States Patent
Robertson et al.

(10) Patent No.: US 7,405,211 B2
(45) Date of Patent: Jul. 29, 2008

(54) THERAPEUTIC MORPHOLINO-SUBSTITUTED COMPOUNDS

(75) Inventors: Alan D. Robertson, Melbourne (AU); Shaun Jackson, Melbourne (AU); Vijaya Kenche, Melbourne (AU); Cindy Yaip, Melbourne (AU); Hishani Parbaharan, Melbourne (AU); Phil Thompson, Melbourne (AU)

(73) Assignee: AstraZeneca AB, Sodertalje (SE)

( * ) Notice: Subject to any disclaimer, the term of this patent is extended or adjusted under 35 U.S.C. 154(b) by 503 days.

(21) Appl. No.: 10/961,062

(22) Filed: Oct. 12, 2004

(65) Prior Publication Data

US 2005/0085471 A1 Apr. 21, 2005

Related U.S. Application Data

(62) Division of application No. 10/181,485, filed as application No. PCT/IB01/00079 on Jan. 24, 2001, now Pat. No. 6,977,255.

(60) Provisional application No. 60/225,826, filed on Aug. 17, 2000, provisional application No. 60/177,351, filed on Jan. 24, 2000.

(51) Int. Cl.
*A61K 31/5377* (2006.01)
*C07D 413/04* (2006.01)

(52) U.S. Cl. .................. 514/232.5; 544/125; 544/151

(58) Field of Classification Search ............. 514/232.5 544/126, 125
See application file for complete search history.

(56) References Cited

FOREIGN PATENT DOCUMENTS

WO WO 90/06921 6/1990
WO WO 91/19707 12/1991

OTHER PUBLICATIONS

Sosnovskikh et al, Russian Chemical Bulletin, International Edition, vol. 50, No. 3, pp. 453-455, Mar. 2001.*
Di Braccio et al., "1,2-fused pyrimidines VII. 3-(Dialkylamino)-1*H*-pyrimido[1,2-*a*]quinolin-1-ones and 2-(dialkylamino)-4*H*-pyrimido[2,1-*a*]isoquinolin-4-ones as antiplatelet compounds," *European Journal of Medicinal Chemistry* (1995), vol. 30, No. 1, pp. 27-38.
Vlahos et al., "A specific inhibitor of phosphatidylinositol 3-kinase, 2-(4-morpholinyl)-8-phenyl-4*H*-1-benzopyran-4-one(LY294002)," *The Journal of Biological Chemistry* (1994), vol. 269, No. 7, pp. 5241-5248.
Morris et al., "A novel synthesis of 2-aminochromones via phosgeniminium salts," *Journal of Organic Chemistry* (1992), vol. 57, pp. 6502-6508.
Morris et al., "Synthesis and biological activity of a potent antiplatelet 7-aminofurochromone," *Bioorganic and Medicinal Chemistry Letters* (1994), vol. 4, No. 21, pp. 2621-2626.
Morris et al., "Synthesis and biological evaluation of antiplatelet 2-aminochromones," *Journal of Medicinal Chemistry* (1993), vol. 36, No. 14, pp. 2026-2032.
Benjamin et al., "2-Aminochromones block human platelet aggregation by inhibiting cyclic AMP-dependent phosphodiesterase leading to reduced platelet phospholipase C activity," *The Journal of Pharmacology and Experimental Therapeutics*, vol. 265, No. 1, pp. 457-462.
Morris et al., "A cyclodehydration route to 2-aminochromones," *Synthetic Communications* (1994), vol. 24, No. 6, pp. 849-858.
Cho et al., "Effects of inclusion complexation on the transepithelial transport of a lipophilic substance in vitro," *Pharmaceutical Research* (1995), vol. 12, No. 4, pp. 560-564.
Supplementary European Search Report for EP 01 90 2568 dated Mar. 6, 2003.
Buchmann, Fred., J., et al., "Syntheses in the Quinoline Series. IV. 2, 4-Disubstituted Quinoline Derivatives," *Journal of the American Chemical Society*, vol. 64, Jun. 1942, pp. 1357-1360, XP002231191.
Chiosis, Gabriela, et al., "LY294002-Geldanamycin Heterodimers as Selective Inhibitors of the P13K and P13K-Related Family," *Bioorganic & Medicinal Chemistry Letters*, 2001, 11, pp. 909-913, XP002231192.
Database Crossfire Beilstein 'Online! Beilstein Institut zur Förderung der Chemischen Wissenchaften, Frankfurt am Main, DE; Database Accession No. BRN 1077329 XP002231193; Abstract, Ingalls, E.A.; Popp, F.D., *Journal of Heterocyclic Chemistry*, vol. 4, 1967, pp. 523-526.
Sosnovskikh et al. "2-Polyfluoroalkylchromones 6. Synthesis of substituted 2-morpholino-2-trifluromethylchroman-4-ones," Russian Chemical Bulletin (2001) 50(3):453-455.

* cited by examiner

*Primary Examiner*—Kamal A. Saeed
(74) *Attorney, Agent, or Firm*—Pepper Hamilton LLP

(57) ABSTRACT

Morpholino-substituted pyridopyrimidine, quinolone, and benzopyranone derivatives inhibit phosphoinositide (PI) 3-kinase, an enzyme that regulates platelet-adhesion processes. As a consequence, the compounds in question have anti-thrombotic activity, as well as other pharmaceutical properties. The compounds claimed are represented by formula (I), (II) and (III). PI 3-kinase generates 3-phosphorylated PI second messengers which stimulate platelet adhesion under blood-flow conditions. Because platelet adhesion is a necessary step in the formation of a thrombus, inhibition by these compounds of PI 3-kinase under such conditions inhibits or prevents thrombus formation. The compounds are useful in treating PI 3-kinase-dependent conditions including cardiovascular diseases such as coronary artery occlusion, stroke, acute coronary syndrome, acute myocardial infarction, vascular restenosis, atherosclerosis, and unstable angina; respiratory diseases such as asthma, chronic obstructive pulmonary diseases (COPD), and bronchitis; inflammatory disorders, neoplasms including cancers such as glioma, prostate cancer, small cell lung cancer, and breast cancer, and diseases linked to disordered white blood cell function, such as autoimmune and inflammatory diseases.

19 Claims, 4 Drawing Sheets

THERAPEUTIC MORPHOLINO-SUBSTITUTED COMPOUNDS

This application is a Divisional of U.S. application Ser. No. 10/181,485 filed Nov. 08, 2002, now U.S. Pat. No. 6,977,255, which is a 371 of PCT/IB01/00079, filed Jan. 24, 2001, which claims benefits of U.S. Provisional Application No. 60/177,351, filed Jan. 24, 2000 and U.S. Provisional Application No. 60/225,826 filed Aug. 17, 2000, now abandoned, the contents of which are incorporated herein.

BACKGROUND OF THE INVENTION

1. Field of the Invention

The present invention is broadly concerned with anti-thrombotic morpholino-substituted compounds and corresponding methods of use. More particularly, the present invention relates to morpholino-substituted pyridopyrimidine, quinolone, and benzopyranone derivatives which inhibit the enzyme phosphoinositide (PI) 3-kinase, and which are useful in treating PI 3-kinase-dependent conditions, including cardiovascular diseases, respiratory diseases, inflammatory disorders, neoplasms such as cancers, and diseases linked to disordered white blood cell function.

2. Description of the Related Art

Cell-adhesion interactions are crucial for a broad range of physiological processes, including inflammation, immunity, and hemostasis. Platelets are specialized adhesive cells which play a fundamental role in the hemostatic process. Upon vascular injury, platelets adhere to specific subendothelial adhesive proteins, such as von Willebrand factor (vWF). The binding of vWF to its specific receptor on the platelet surface, glycoprotein (GP) Ib/V/IX, induces platelet activation and cytoskeletal reorganization. These cytoskeletal changes result in filopodial extension and the formation of lamellipodial sheets, which are essential processes for platelet spreading and the formation of the primary hemostatic platelet plug.

An exaggerated platelet adhesion response at sites of atherosclerotic plaque rupture commonly leads to the formation of vaso-occlusive platelet thrombi. The formation of these thrombi in the coronary or cerebral circulation leads to heart attacks and strokes, respectively, which combined represent the leading causes of death in the industrialized world. Platelet thrombus formation also leads to a number of other clinical states including unstable angina, sudden death, transient ischemic attacks, amaurosis fugax, and acute ischemia of limbs and internal organs.

Undesirable thrombosis also may be associated, however, with invasive medical procedures such as cardiac surgery (e.g., angioplasty), abdominothoracic surgery, arterial surgery, deployment of an implementation (e.g., a stent or catheter), and endarterectomy. Furthermore, thrombosis may accompany various thromboembolic disorders and coagulopathies such as a stroke, pulmonary embolism (e.g., atrial fibrillation with embolization) and disseminated intravascular coagulation. An unwanted thrombus also can arise from manipulation of body fluids, as occurs in the context of blood transfusion or fluid sampling, as well as in procedures involving extracorporeal circulation (e.g., cardiopulmonary bypass surgery) and dialysis.

Anti-coagulants and anti-platelet agents are frequently used to alleviate thrombosis. Blood clotting can be minimized or eliminated in many instances by administering a suitable anti-coagulant, including one or more of a coumarin derivative (e.g., warfarin and dicumarol) or a charged polymer (e.g., heparin, hirudin or hirulog), or through the use of an anti-platelet agent (e.g, aspirin, clopidogrel, ticlopidine, dipyridamole, or one of several GPIIb/IIIa receptor antagonists). But anti-coagulants and platelet inhibitors can have side effects such as hemorrhaging, re-occlusion, "white-clot" syndrome, irritation, birth defects, thrombocytopenia, and hepatic dysfunction. Moreover, long-term administration of anti-coagulants and platelet inhibitors can particularly increase risk of life-threatening illness or hemorrhage.

SUMMARY OF THE INVENTION

To avoid the aforementioned drawbacks in using anti-coagulants or anti-platelet drugs to inhibit or prevent undesirable thrombosis, it is an object of the present invention to provide an anti-thrombotic morpholino-substituted pyridopyrimidine derivative having the following formula:

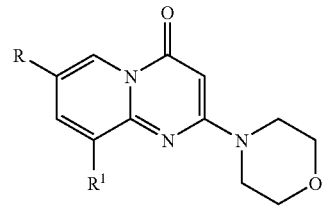

R is H, OH, F, Cl, Br, I, $C_1$-$C_6$ alkyl, aryl or $(CH_2)_n$-aryl;

$R^1$ is H, OH, F, Cl, Br, I, $C_1$-$C_6$ alkyl, $C_3$-$C_6$ cycloalkyl, CH=CH-aryl, C≡C-aryl, $(CHR^3)_n$-aryl, $NR^3$—$C_1$-$C_6$ alkyl, $NR^3$-cycloalkyl, $NR^3$—$(CHR^3)_n$-aryl, $(CHR^3)_n$—$NR^3$-aryl, $(CHR^3)_n$—$NR^3$-alkyl, $(CHR^3)_n$—$NR^3$-cycloalkyl, $(CHR^3)_n$—O-aryl, $(CHR^3)_n$—O-alkyl, $(CHR^3)_n$—O-cycloalkyl, O—$(CHR^3)_n$-aryl, S—$(CHR^3)_n$-aryl, or CO-aryl, wherein n is 0, 1, or 2 and alkyl, cycloalkyl or aryl is optionally substituted with F, Cl, Br, I, CN, $CO_2H$, $CO_2R^3$, $NO_2$, $CF_3$, substituted or unsubstituted $C_1$-$C_6$ alkyl, substituted or unsubstituted cycloalkyl, substituted or unsubstituted aryl, $OCF_3$, $OR^3$, $OSO_2$-aryl, substituted or unsubstituted amine, $NHCOR^3$, $NHSO_2R^3$, $CONHR^3$, or $SO_2NHR^3$; and $R^3$ is H, or substituted or unsubstituted $C_1$-$C_6$alkyl, substituted or unsubstituted aryl.

Preferred groups represented by $R^1$ include —$CH_3$, Br,

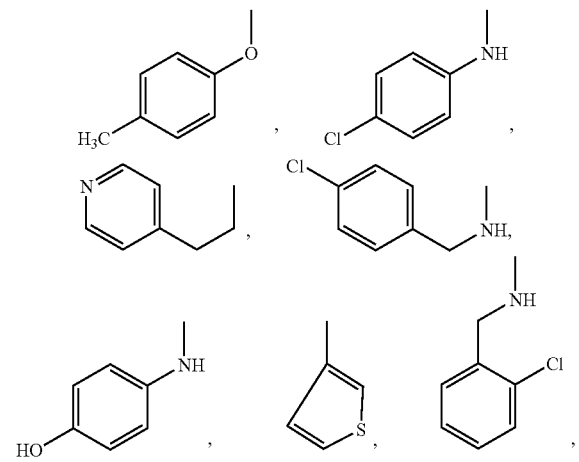

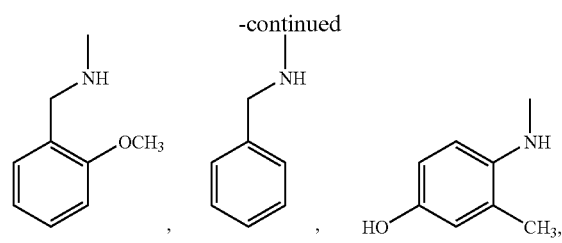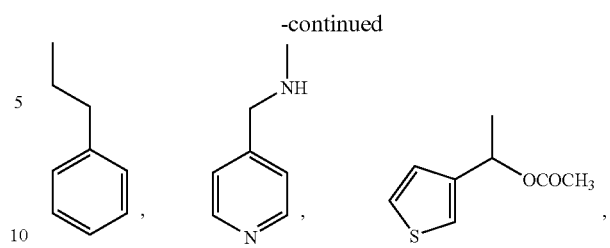
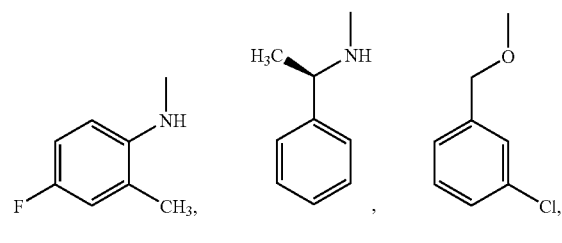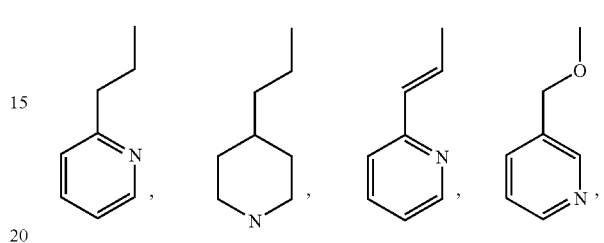
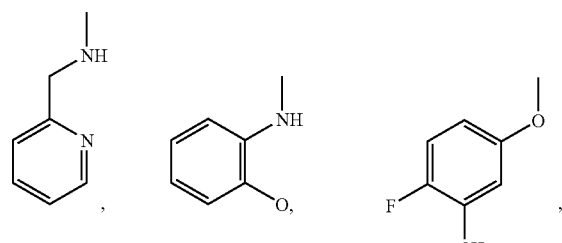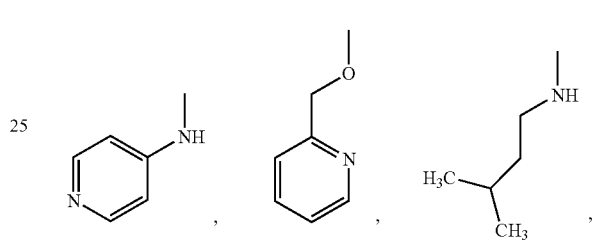
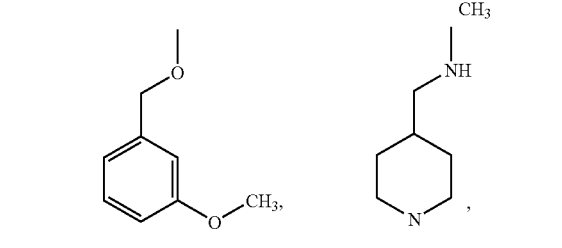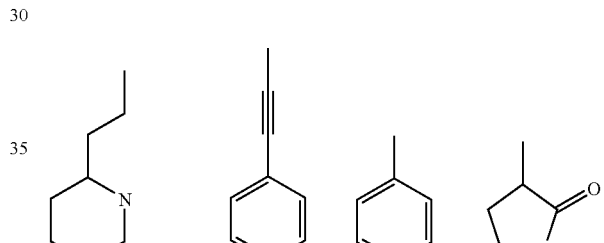
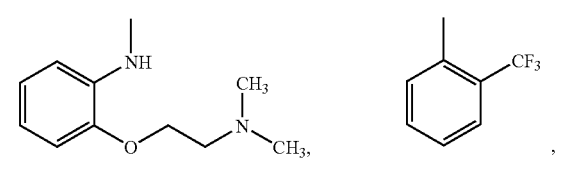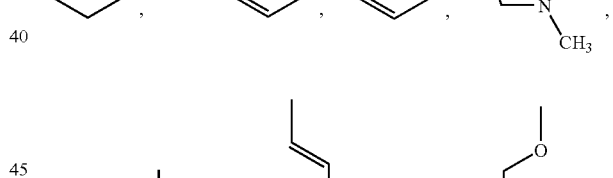
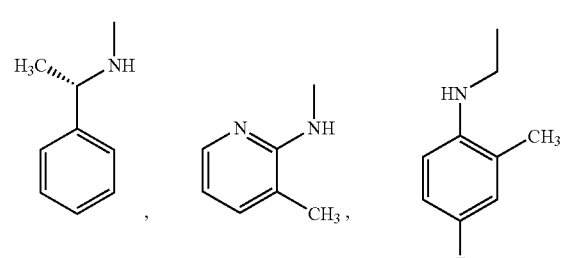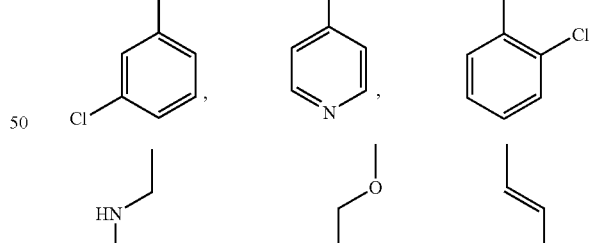
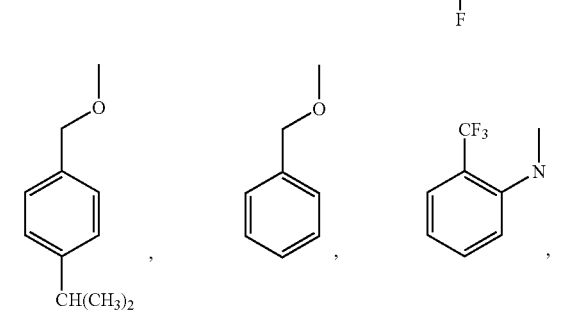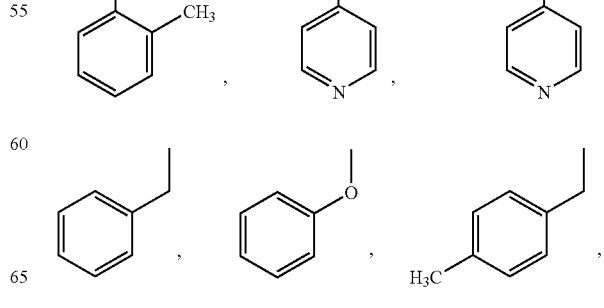

-continued

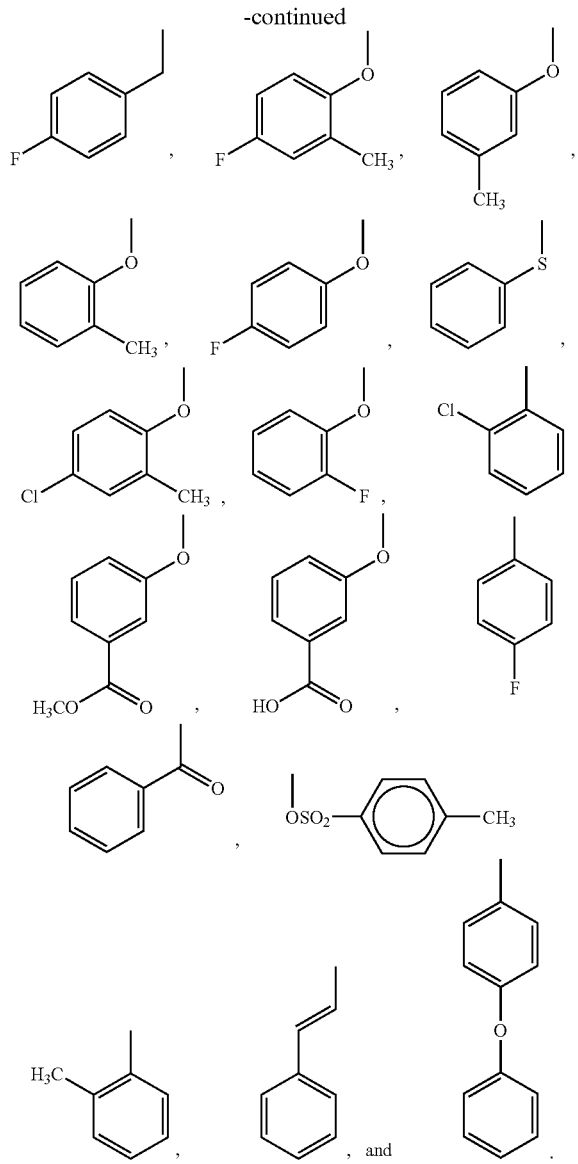

It is another object of the present invention to provide an anti-thrombotic morpholino-substituted quinolone derivative having the following formula:

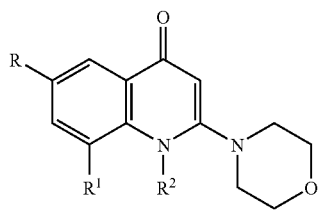

R and $R^2$ are independently H, OH, F, Cl, Br, I, $C_1$-$C_6$ alkyl, aryl or $(CH_2)_n$-aryl;

$R^1$ is H, OH, F, Cl, Br, I, $C_1$-$C_6$ alkyl, $C_3$-$C_6$ cycloalkyl, CH=CH-aryl, C≡C-aryl, $(CHR^3)_n$-aryl, $NR^3$—$C_1$-$C_6$ alkyl, $NR^3$-cycloalkyl, $NR^3$—$(CHR^3)_n$-aryl, $(CHR^3)_n$-$NR^3$-aryl, $(CHR^3)_n$—$NR^3$-alkyl, $(CHR^3)_n$—$NR^3$-cycloalkyl, $(CHR^3)_n$—O-aryl, $(CHR^3)_n$—O-alkyl, $(CHR^3)_n$—O-cycloalkyl, O—$(CHR^3)_n$-aryl, S—$(CHR^3)_n$-aryl, or CO-aryl, wherein n is 0, 1, or 2 and alkyl, cycloalkyl or aryl is optionally substituted with F, Cl, Br, I, CN, $CO_2H$, $CO_2R^3$, $NO_2$, $CF_3$, substituted or unsubstituted $C_1$-$C_6$ alkyl, substituted or unsubstituted cycloalkyl, substituted or unsubstituted aryl, $OCF_3$, $OR^3$, $OSO_2$-aryl, substituted or unsubstituted amine, $NHCOR^3$, $NHSO_2R^3$, $CONHR^3$, or $SO_2NHR^3$; and $R^3$ is H, or substituted or unsubstituted $C_1$-$C_6$alkyl, substituted or unsubstituted aryl.

Preferred groups represented by $R^1$ include —$CH_3$, Br,

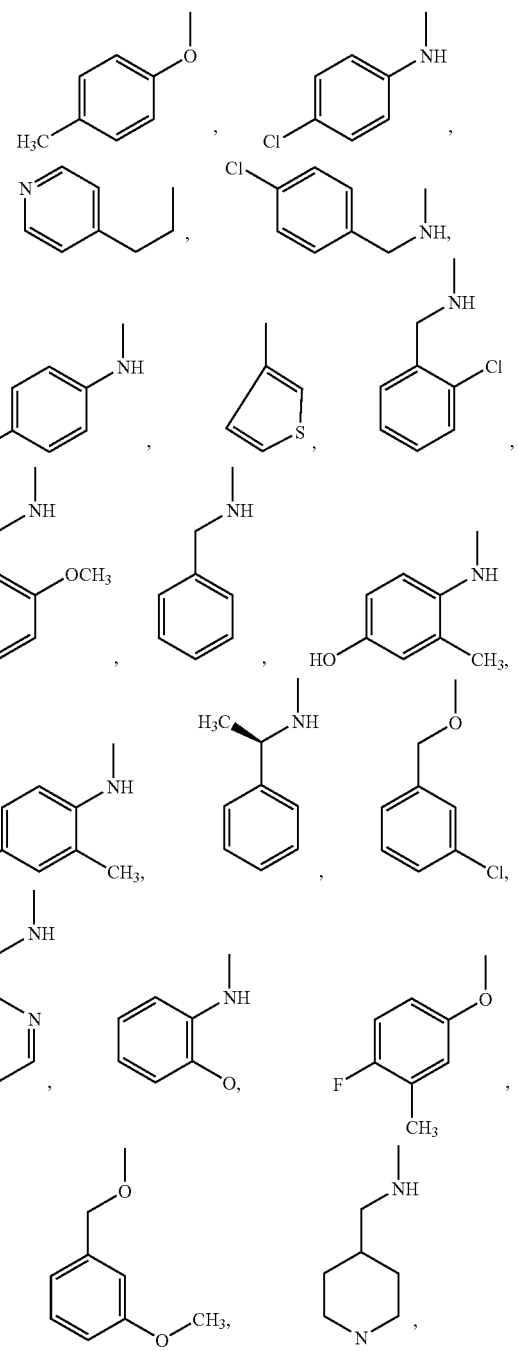

-continued
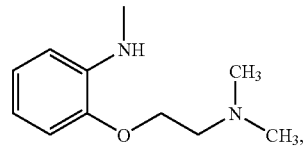 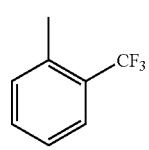 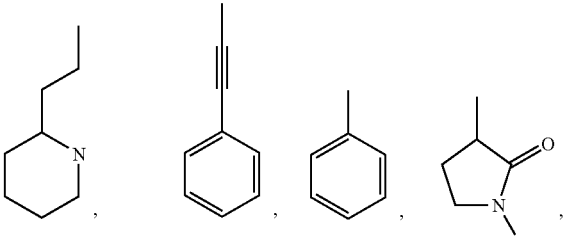
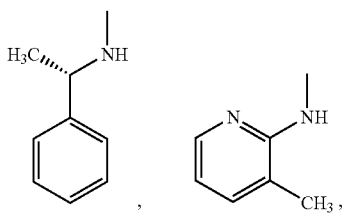 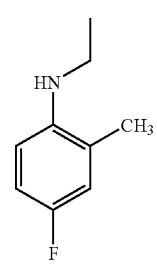 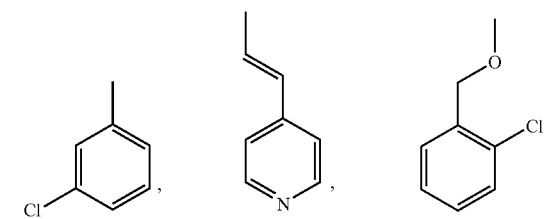
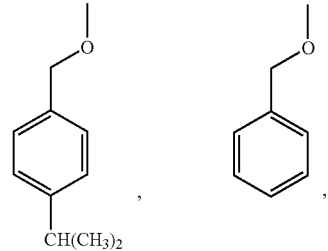 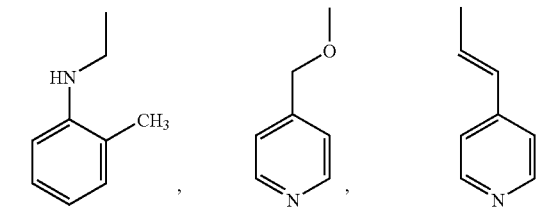
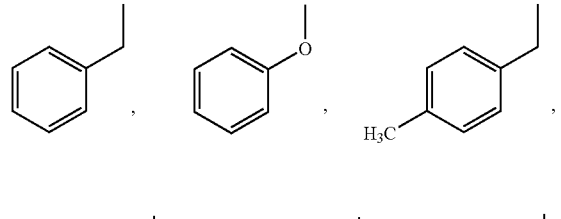
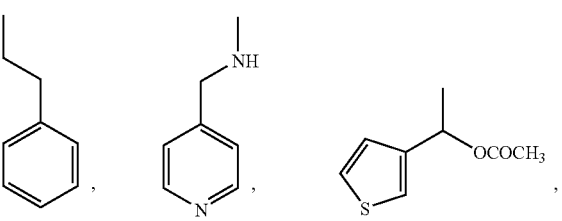
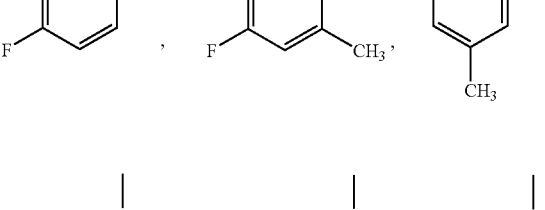
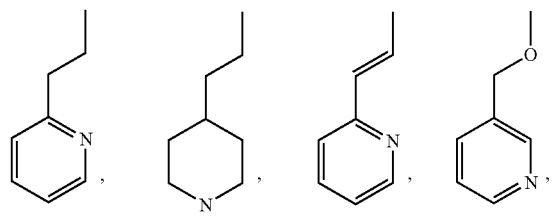
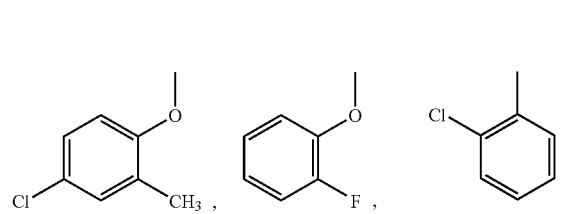
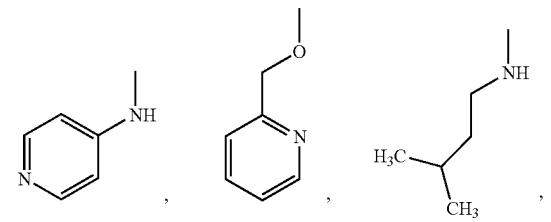

-continued

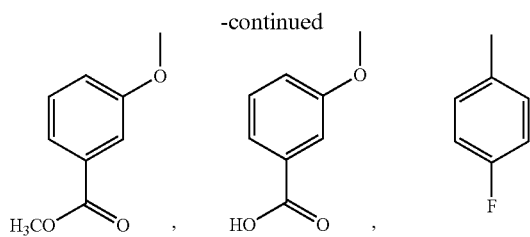

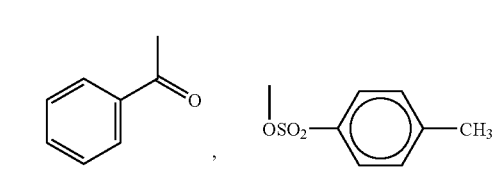

It is yet another object of the present invention to provide an anti-thrombotic morpholino-substituted benzopyranone derivative having the following formula:

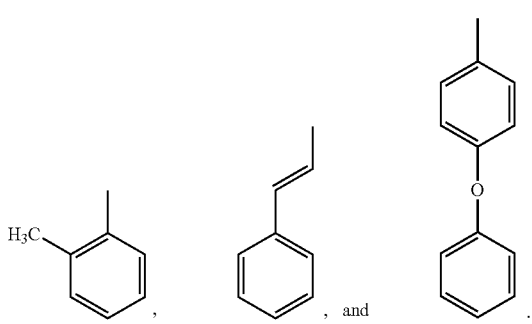

R is H, OH, F, Cl, Br, I, $C_1$-$C_6$ alkyl, aryl or $(CH_2)_n$-aryl;
$R^1$ and $R^2$ are independently H, OH, F, Cl, Br, I, $C_1$-$C_6$ alkyl, $C_3$-$C_6$ cycloalkyl, CH=CH-aryl, C≡C-aryl, $(CHR^3)_n$-aryl, $NR^3$—$C_1$-$C_6$ alkyl, $NR^3$-cycloalkyl, $NR^3$—$(CHR^3)_n$-aryl, $(CHR^3)_n$—$NR^3$-aryl, $(CHR^3)_n$—$NR^3$-alkyl, $(CHR^3)_n$—$NR^3$-cycloalkyl, $(CHR^3)_n$—O-aryl, $(CHR^3)_n$—O-alkyl, $(CHR^3)_n$—O-cycloalkyl, O—$(CHR^3)_n$-aryl, S—$(CHR^3)_n$-aryl, or CO-aryl, wherein n is 0,1, or 2 and alkyl, cycloalkyl or aryl is optionally substituted with F, Cl, Br, I, CN, $CO_2H$, $CO_2^3$, $NO_2$, $CF_3$, substituted or unsubstituted $C_1$-$C_6$ alkyl, substituted or unsubstituted cycloalkyl, substituted or unsubstituted aryl, $OCF_3$, $OR^3$, $OSO_2$-aryl, substituted or unsubstituted amine, $NHCOR^3$, $NHSO_2R^3$, $CONHR^3$, or $SO_2NHR^3$; and $R^3$ is H, or substituted or unsubstituted $C_1$-$C_6$alkyl, substituted or unsubstituted aryl.

Preferred groups represented by $R^1$ include —$CH_3$, Br,

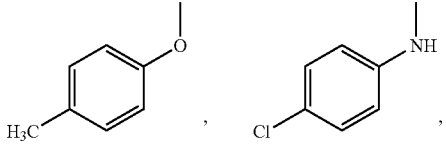

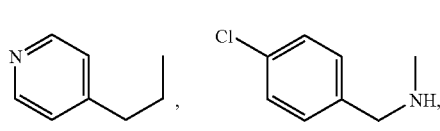

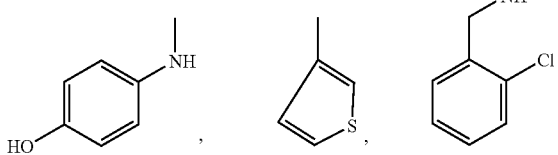

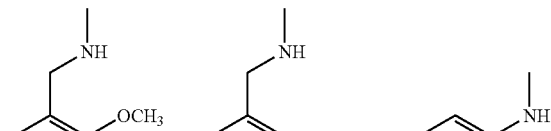

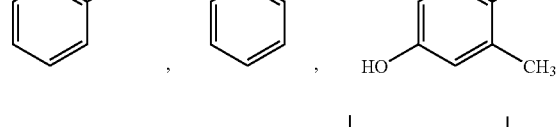

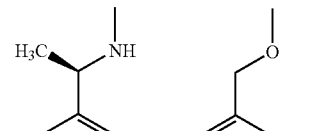

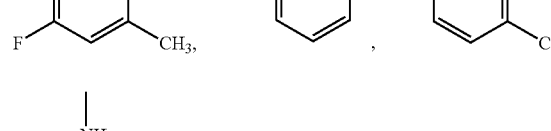

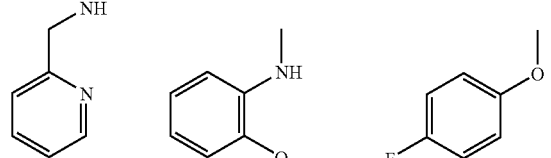

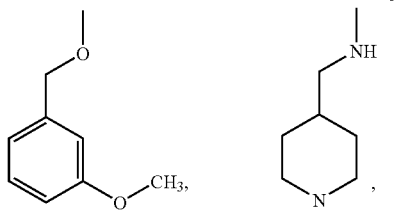

-continued

-continued
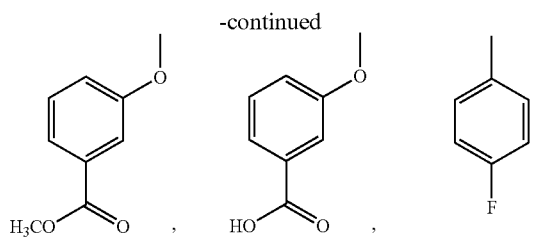
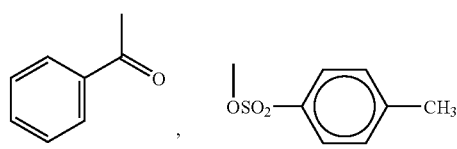
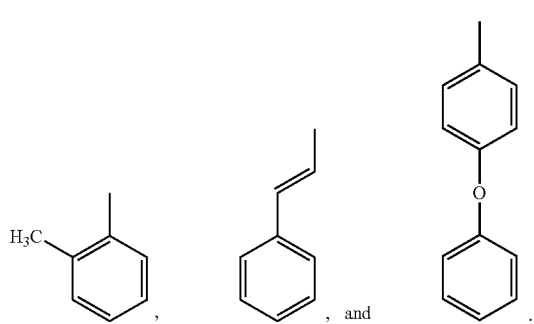
Preferred compounds of the morpholino-substituted pyridopyrimidine derivatives are shown in Table I.
TABLE I
| TGX | STRUCTURE |
|---|---|
| TGX-167B | 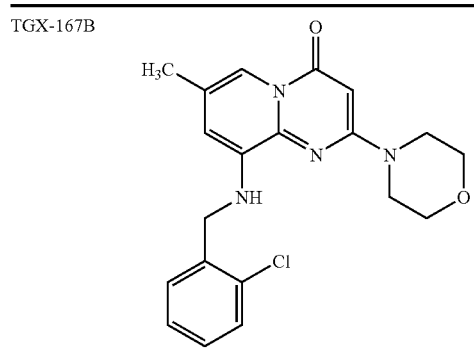 |
| TGX-137 | 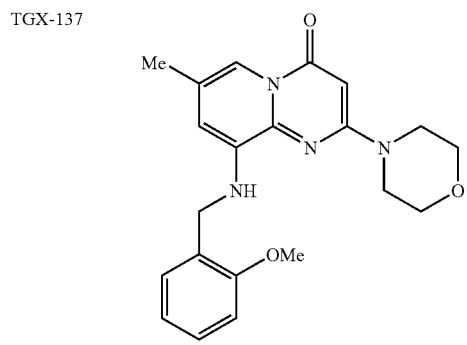 |
TABLE I-continued
| TGX | STRUCTURE |
|---|---|
| TGX-126 | 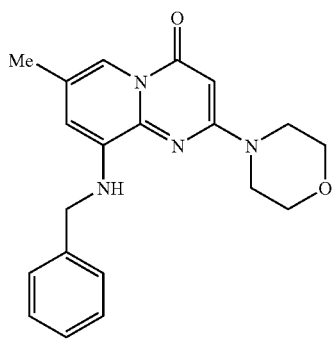 |
| TGX-174 | 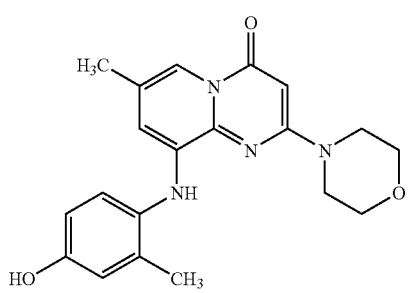 |
| TGX-101 | 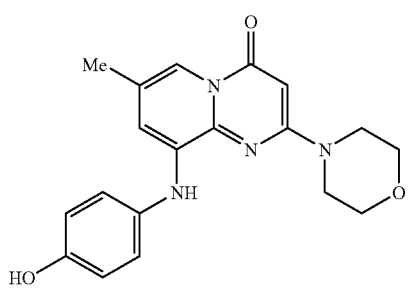 |
| TGX-170 | 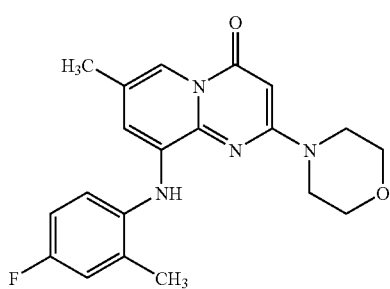 |

TABLE I-continued
| TGX | STRUCTURE |
|---|---|
| TGX-123 | 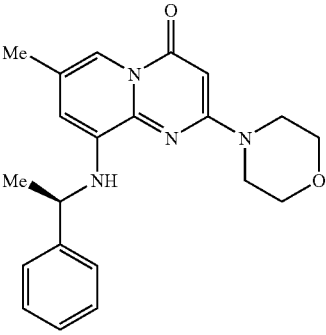 |
| TGX-176 | 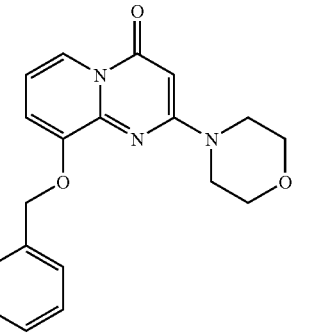 |
| TGX-161 | 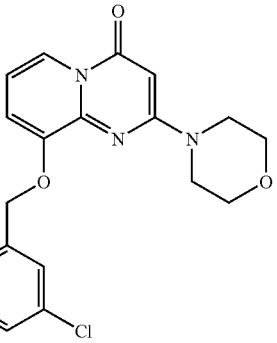 |
| TGX-131 | 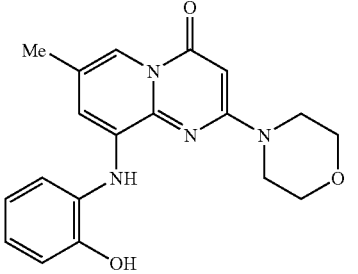 |
| TGX-130 | 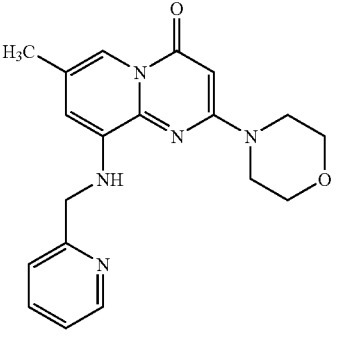 |
| TGX-168 | 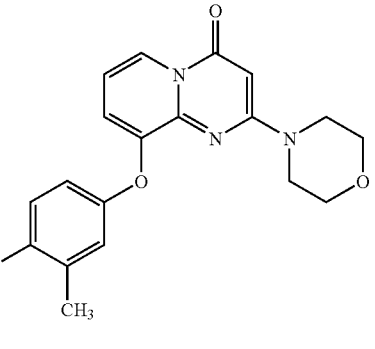 |

TABLE I-continued
| TGX | STRUCTURE |
|---|---|
| TGX-163 | 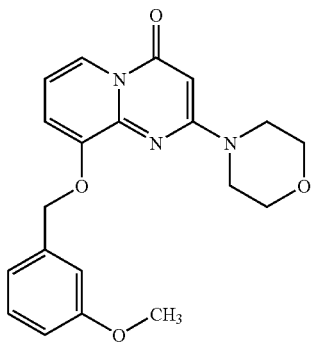 |
| TGX-141 | 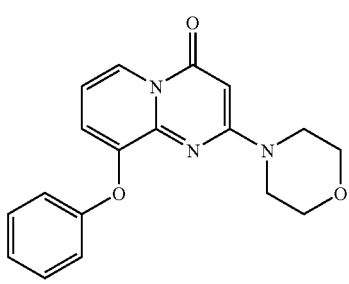 |
| TGX-139 | 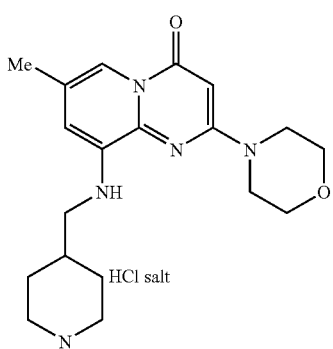 |
| TGX-108 | 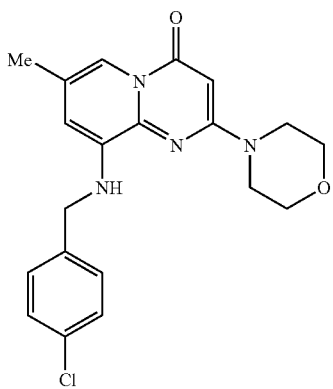 |
TABLE I-continued
| TGX | STRUCTURE |
|---|---|
| TGX-107 | 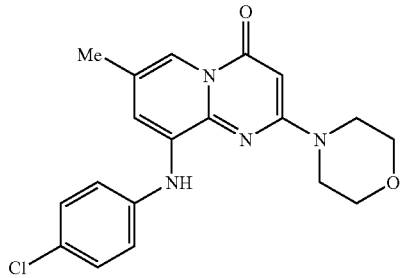 |
| TGX-040 | 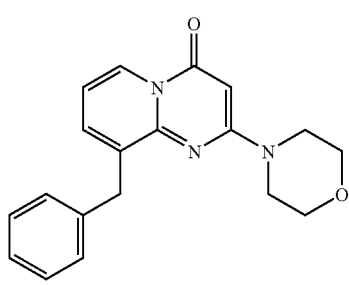 |
| TGX-162 | 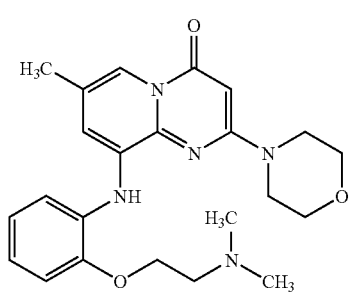 |
| TGX-142 | 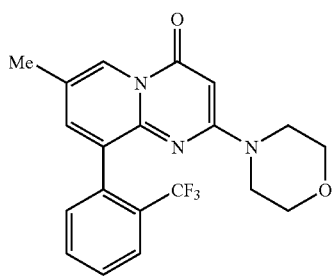 |

TABLE I-continued
| TGX | STRUCTURE |
|---|---|
| TGX-124 | 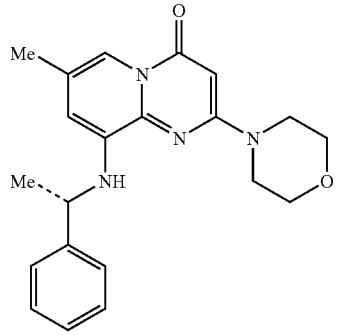 |
| TGX-179 | 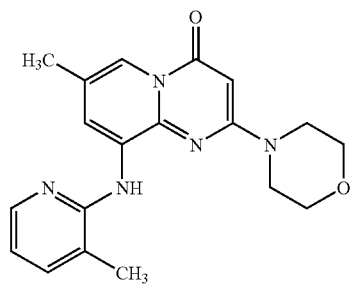 |
| TGX-087 | 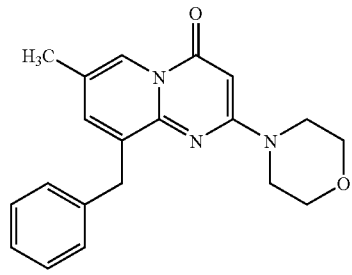 |
| TGX-169 | 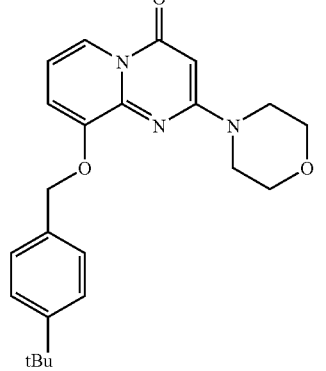 |
TABLE I-continued
| TGX | STRUCTURE |
|---|---|
| TGX-147 | 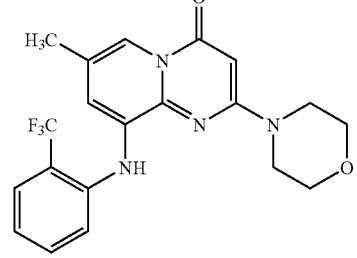 |
| TGX-093 | 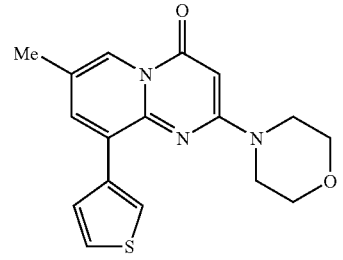 |
| TGX-083 | 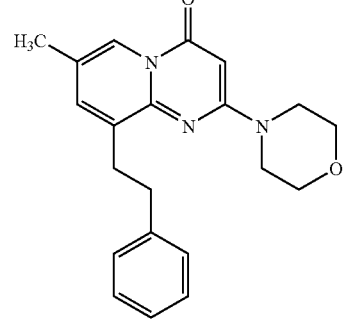 |
| TGX-112 | 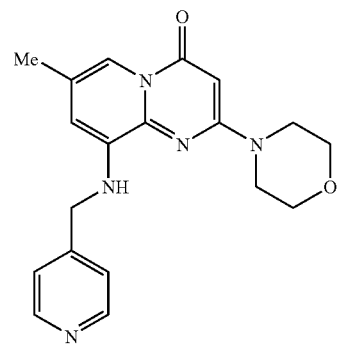 |

TABLE I-continued

| TGX | STRUCTURE |
|---|---|
| TGX-100 | 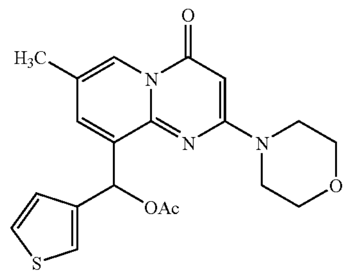 |
| TGX-098 | 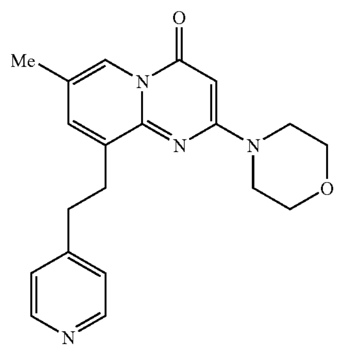 |
| TGX-096 | 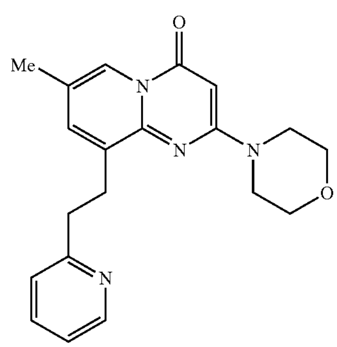 |
| TGX-095 | 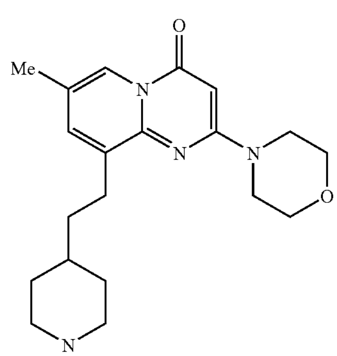 |
| TGX-091 | |
| TGX-140 | |
| TGX-120 | |
| TGX-148 | |

TABLE I-continued
| TGX | STRUCTURE |
|---|---|
| TGX-110 | 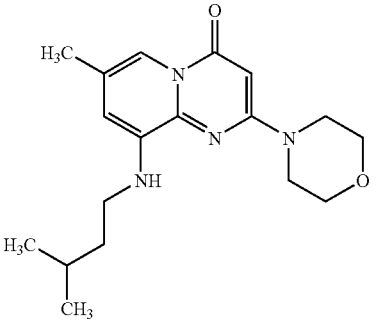 |
| TGX-097 | 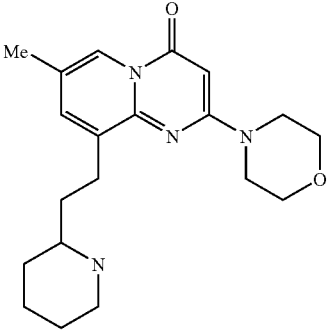 |
| TGX-069 | 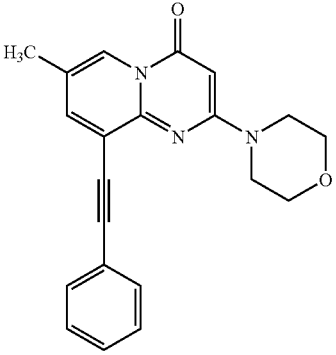 |
| TGX-041 | 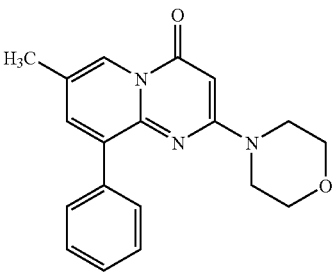 |
TABLE I-continued
| TGX | STRUCTURE |
|---|---|
| TGX-037 | 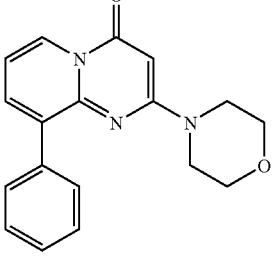 |
| TGX-025 | 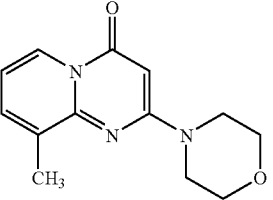 |
| TGX-066 | 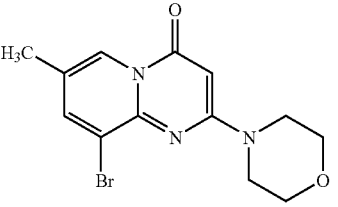 |
| TGX-109 | 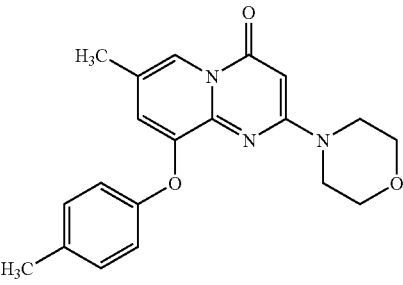 |
| TGX-153 | 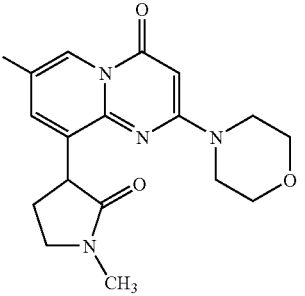 |

TABLE I-continued
| TGX | STRUCTURE |
|---|---|
| TGX-024 | 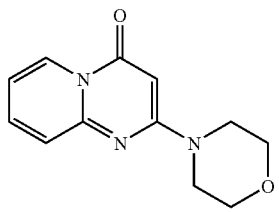 |
| TGX-033 | 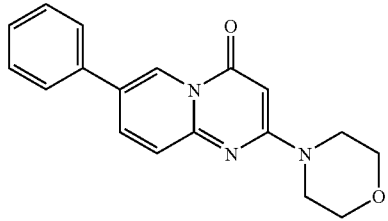 |
| TGX-026 | 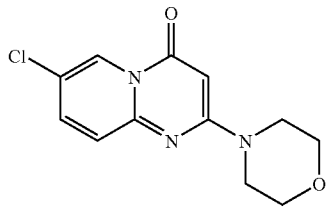 |
| TGX-064 | 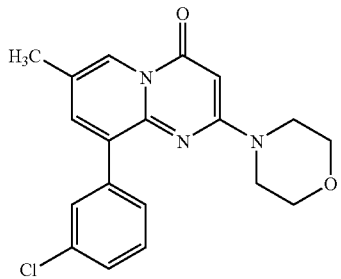 |
| TGX-089 | 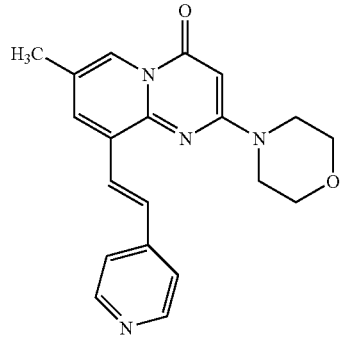 |
| TGX-183 | 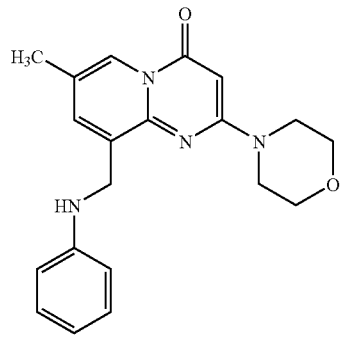 |
| TGX-186 | 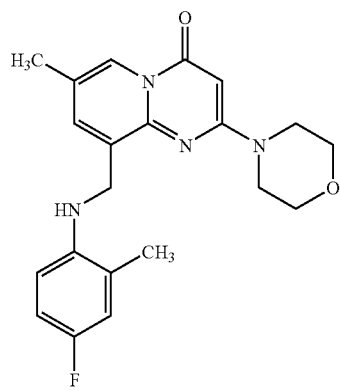 |
| TGX-177 | 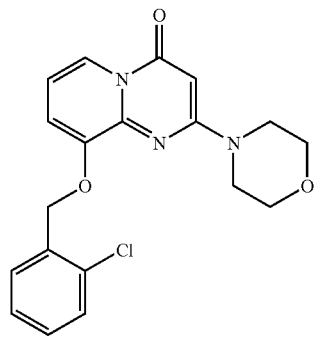 |

TABLE I-continued
| TGX | STRUCTURE |
|---|---|
| TGX-185 | 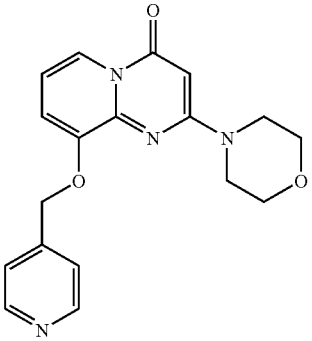 |
Preferred compounds of the morpholino-substituted quinolone derivatives are shown in Table II.
TABLE II
| TGX | STRUCTURE |
|---|---|
| TGX-155 | 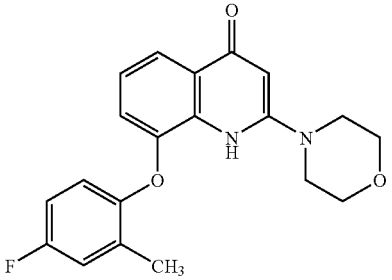 |
| TGX-127 | 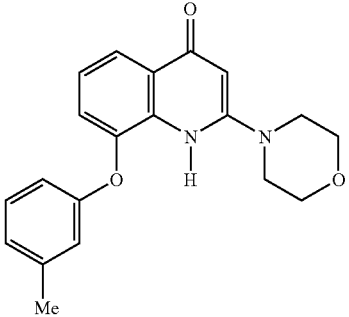 |
| TGX-115 | 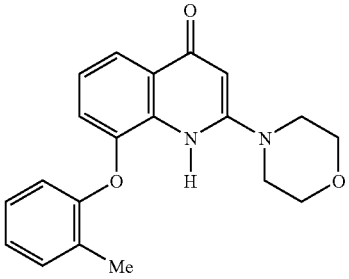 |
| TGX-121 | 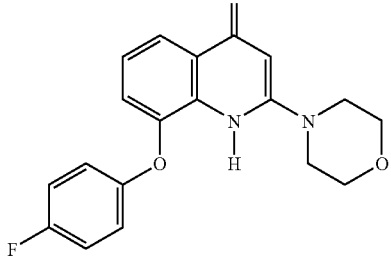 |
| TGX-111 | 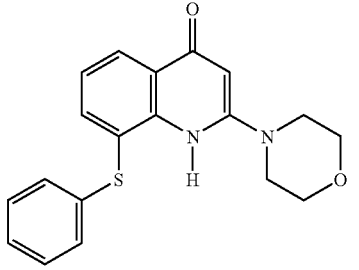 |
| TGX-084 | 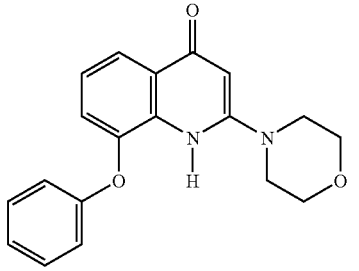 |
| TGX-180 | 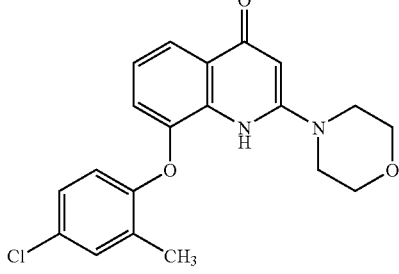 |
| TGX-143 | 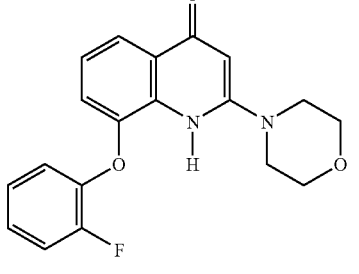 |

TABLE II-continued
| TGX | STRUCTURE |
|---|---|
| TGX-113 | 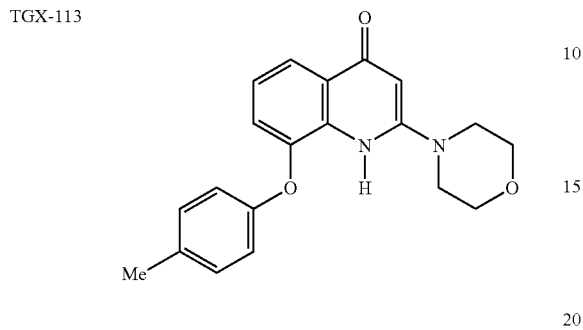 |
| TGX-149 | 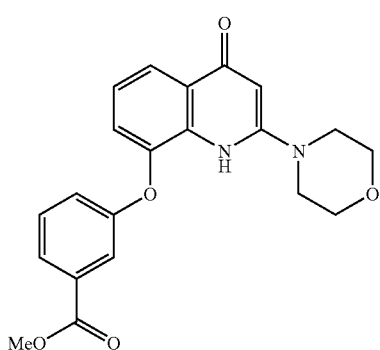 |
| TGX-152 | 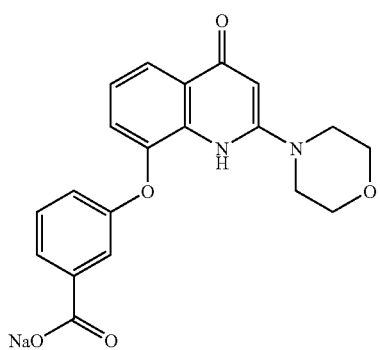 |
TABLE II-continued
| TGX | STRUCTURE |
|---|---|
| TGX-151 | 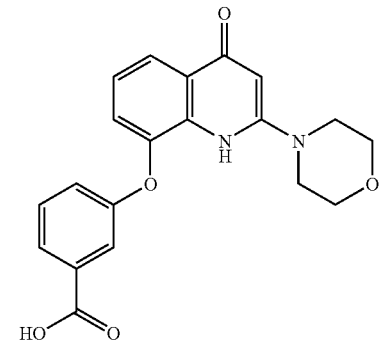 |
| TGX-171 | 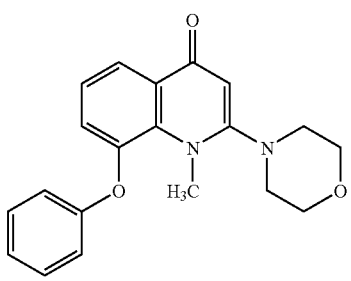 |
| TGX-099 | 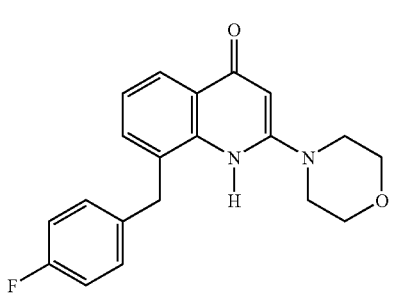 |

TABLE II-continued
| TGX | STRUCTURE |
|---|---|
| TGX-106 | 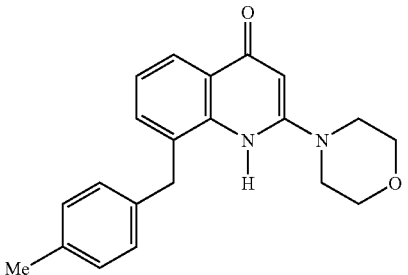 |
| TGX-057 | 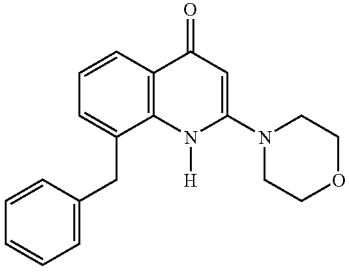 |
| TGX-070 | 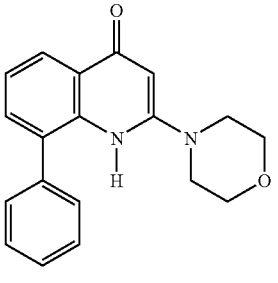 |
| TGX-077 | 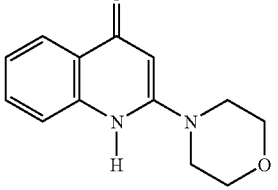 |
| TGX-071 | 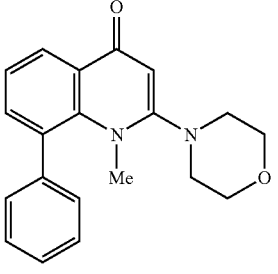 |
TABLE II-continued
| TGX | STRUCTURE |
|---|---|
| TGX-086 | 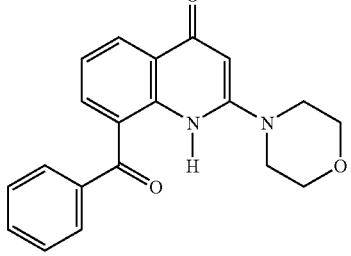 |
| TGX-078 | 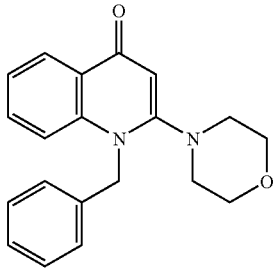 |
| TGX-074 | 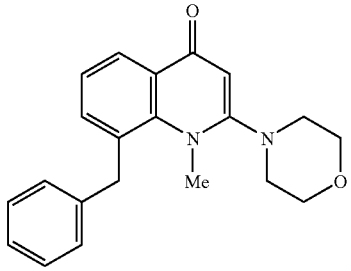 |
| TGX-138 | 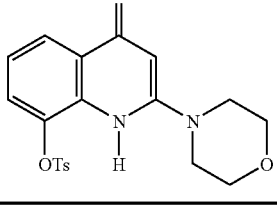 |
Preferred compounds of the morpholino-substituted benzopyranone derivatives are shown in Table III.
TABLE III
| TGX | STRUCTURE |
|---|---|
| TGX-134 | 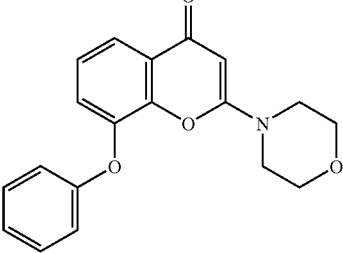 |

TABLE III-continued

| TGX | STRUCTURE |
|---|---|
| TGX-102 | 8-benzyloxy-2-morpholino-4H-chromen-4-one |
| TGX-90 | 8-benzyl-2-morpholino-4H-chromen-4-one |
| TGX-135 | 2-morpholino-8-(2-trifluoromethylphenyl)-4H-chromen-4-one |
| TGX-173 | 8-(4-fluoro-3-methylphenoxy)-2-morpholino-4H-chromen-4-one |
| TGX-165 | 8-(4-fluorophenyl)-2-morpholino-4H-chromen-4-one |
| TGX-146 | 8-(2-chlorophenyl)-2-morpholino-4H-chromen-4-one |
| TGX-132 | 2-morpholino-8-(pyridin-3-ylmethoxy)-4H-chromen-4-one · CF$_3$COOH |
| TGX-103 | 7-benzyloxy-2-morpholino-4H-chromen-4-one |
| TGX-136 | 2-morpholino-7-phenyl-4H-chromen-4-one |
| TGX-160 | 8-methyl-2-morpholino-7-phenoxy-4H-chromen-4-one |

TABLE III-continued
| TGX | STRUCTURE |
|---|---|
| TGX-145 | 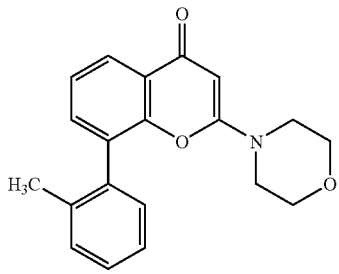 |
| TGX-144 | 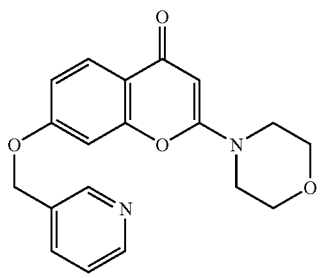 |
| TGX-158 | 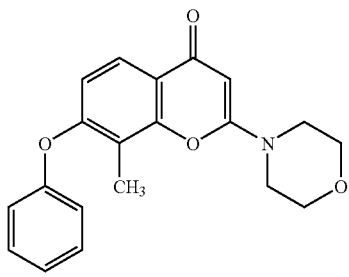 |
| TGX-157 | 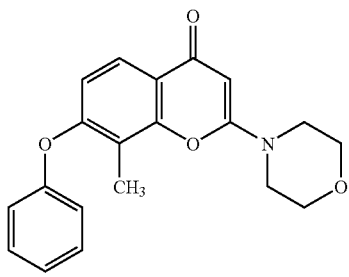 |
| TGX-117 | 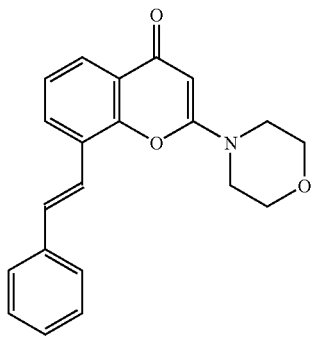 |
TABLE III-continued
| TGX | STRUCTURE |
|---|---|
| TGX-159 | 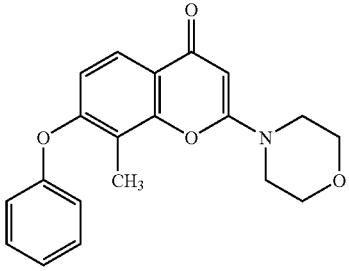 |
| TGX-154 | 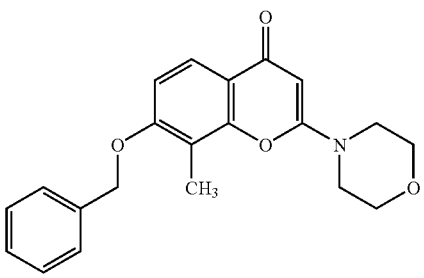 |
| TGX-118 | 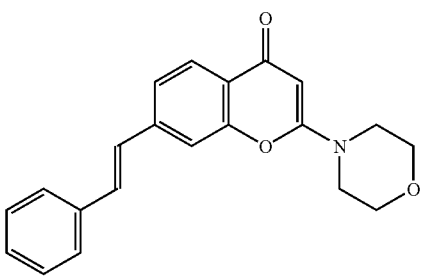 |
| TGX-125 | 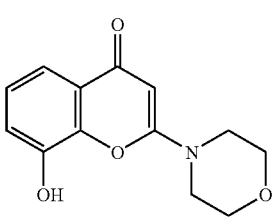 |
| TGX-129 | 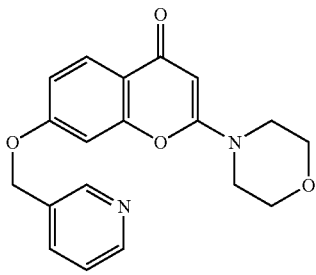 |

TABLE III-continued

| TGX | STRUCTURE |
|---|---|
| TGX-182 | 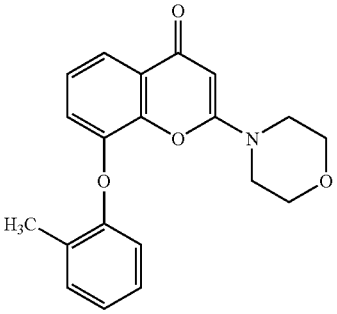 |
| TGX-184 | 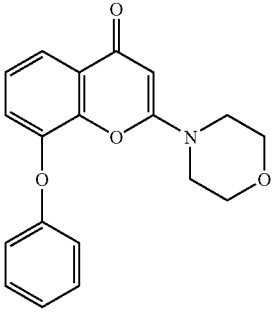 |
| TGX-166 | 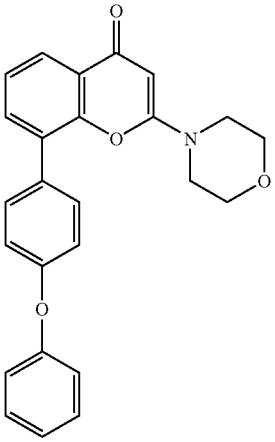 |

It is another object of the present invention to provide a method for inhibiting PI 3-kinase in a patient, comprising administering to the patient an amount of one of the compounds of the present invention, wherein the amount is effective in inhibiting the phosphoinositide 3-kinase in the patient.

It is still another object of the present invention to provide a method for preventing or treating cardiovascular disease, such as coronary artery occlusion, stroke, acute coronary syndrome, acute myocardial infarction, restenosis, atherosclerosis, and unstable angina, by administering an effective amount of one of the compounds of the present invention to a patient in need thereof. Similarly, the present invention contemplates preventing or treating respiratory disease, for example, asthma, chronic obstructive pulmonary disease, and brochitis, or a cancer condition, such as a glioma, prostate cancer, small cell lung cancer, and breast cancer, by administering an effective amount of one of the compounds of the present invention to a patient in need thereof.

Another object of the present invention relates to a method for preventing or treating disease linked to disordered white blood cell function, e.g., autoimmune disease and inflammatory disease, by administering, to a patient in need thereof, an effective amount of one of the compounds of the present invention.

Advantageously, in the present methods for preventing or treating a disease condition, the effective amount of one of the present compounds is administered in the form of a dose. In preferred embodiments, the dose is preferably in the form of a tablet (e.g., a tablet formulated for oral, sublingual, and buccal administration), capsule (e.g., a capsule containing powder, liquid, or a controlled-release formulation), intravenous formulation, intranasal formulation, formulation for muscular injection, syrup, suppository, aerosol, buccal formulation, transdermal formulation, or pessary. Preferably, the dose contains from about 5 to about 500 mg of the compound, and more preferably contains from about 25 to about 300 mg of the compound.

DETAILED DESCRIPTION OF THE PREFERRED EMBODIMENT

Figure 1:
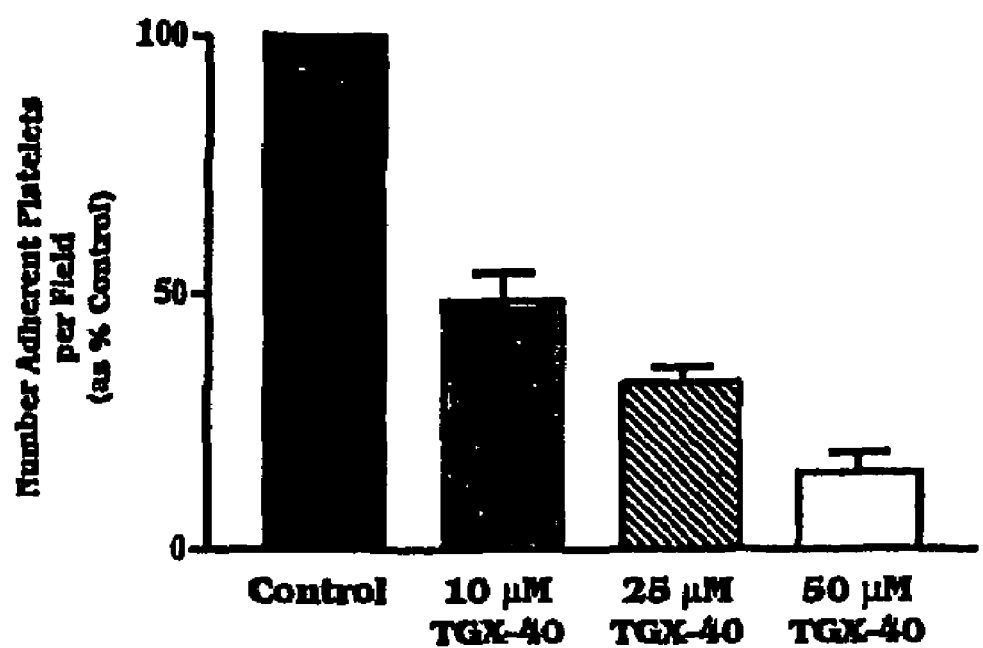
FIG. 1 shows a bar graph illustrating the effect, in a flow-based reconstitution assay, of various concentrations of TGX-40 on the adhesion of platelets to vWf-coated glass microslides.

In the context of this description, the term "alkyl" refers to straight or branched saturated aliphatic hydrocarbon radical. Preferably, the alkyl group has 1 to 6 carbons and optionally substitued with one or more groups selected from halogen such as F, Cl, Br or I; CN; $CO_2R_3$; $NO_2$; $CF_3$; substituted or unsubstituted $C_1$-$C_6$ alkyl; substituted or unsubstituted $C_3$-$C_6$ cycloalkyl; substituted or unsubstituted aryl; $OCF_3$, $OR_3$, substituted or unsubstituted amine; $NHCOR_3$; $NHSO_2R_3$; $CONHR_3$; or $SO_2NHR_3$, wherein $R_3$ is H, substituted or unsubstituted $C_1$-$C_6$ alkyl, substituted or unsbustituted aryl.

The term "cycloalkyl" refers to non-heterocyclic (i.e., carbocyclic) or heterocyclic ring. Exemplary of non-heterocyclic ring in this regard is substituted or unsubstituted cyclopropane, cyclobutane, cyclopentane, cyclohexane, cyclohexadione, cyclopentanedione, quinone and the like. Suitable heterocycloalkyl groups include substituted or unsubstituted pyrrolidine, piperidine, piperazine, 2-piperidone, azacyclohexan-2-one and morpholine groups. The cycloalkyl group is optionally substituted at one or more positions with halogen such as F, Cl, Br or I; CN; $CO_2R_3$; $NO_2$; $CF_3$, substituted or unsubstituted $C_1$-$C_6$ alkyl; substituted or unsubstituted $C_3$-$C_6$ cycloalkyl; substituted or unsubstituted aryl; $OCF_3$, $OR_3$, substituted or unsubstituted amine; $NHCOR_3$; $NHSO_2R_3$; $CONHR_3$; or $SO_2NR$, wherein $R_3$ is H, substituted or unsubstituted $C_1$-$C_6$ alkyl, substituted or unsbustituted aryl.

The term "aryl" refers to an aromatic or heteroaromatic rings. Examples of an aryl group are pyrrolidine, thiophene, pyrrole, pyrazole, imidazole, 1,2,3-triazole, 1,2,4-triazole, oxazole, isoxazole, thiazole, isothiazole, furan, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, tetrazole, benzene, pyridine, pyridazine, pyrimidine, pyrazine, triazine, indene, naphthalene, indole, isoindole, indolizine, benzofuran, benzothiophene, indazole, benzimidazole, benzthiazole, purine, quinolizine, quinoline, isoquinoline, cinnoline, phthalazine, quinazoline, quinoxaline, naphthyridine, pteridine, fluorene, carbazole, carboline, acridine, phenazine, and anthracene. The aryl group is optionally substituted at one or more positions with halogen such as F, Cl, Br or I; CN; $CO_2R_3$; $NO_2$; $CF_3$, substituted or unsubstituted $C_1$-$C_6$ alkyl; substituted or unsubstituted $C_3$-$C_6$ cycloalkyl; substituted or unsubstituted aryl; $OCF_3$, OR, substituted or unsubstituted amine; $NHCOR_3$; $NHSO_2R_3$; $CONHR_3$; or $SO_2NHR_3$, wherein $R_3$ is H, substituted or unsubstituted $C_1$-$C_6$ alkyl, substituted or unsbustituted aryl.

The morpholino-substituted compounds of the present invention have been found to inhibit the lipid signalling enzyme PI 3-kinase, which regulates platelet-adhesion processes under blood-flow conditions, and therefore to display anti-thrombotic activity, as well as other pharmacological properties elaborated below. PI 3-kinase generates 3-phosphorylated PI second messengers, including phosphatidylinositol-3-phosphate (PI(3)P), phosphatidylinositol-3,4-bisphosphate (PI(3,4)$P_2$), and phosphatidylinositol-3,4,5-triphosphate (PI(3,4,5)$P_3$). These second messengers are thought to regulate a diverse range of cellular phenomena, including glucose transport, apoptosis prevention, vesicular trafficking, cell growth, and cytoskeletal reorganization.

To the inventors' knowledge, there are no published reports on the effects of PI 3-kinase inhibitors on platelet adhesion under pathophysiologically relevant flow conditions. Nevertheless, it has been discovered that PI 3-kinase plays a critical role in regulating platelet adhesion, particularly under conditions of physiological flow. Thus, treatment of platelets with the compounds of the present invention inhibit the formation of the phosphorylated lipid products of PI 3-kinase, PI(3)P, PI(3,4)$P_2$, and PI(3,4,5)$P_3$, effecting a marked reduction in platelet adhesion to a vWf matrix under flow conditions. This reduction in platelet adhesion is associated with abnormal platelet spreading and thrombus formation. Because shear-dependent platelet adhesion and activation is important in arterial thrombus formation, PI 3-kinase is an important target for therapeutic intervention in cardiovascular diseases generally.

These inhibitors of PI 3-kinase also have potential therapeutic uses in a variety of other disease states. For example, PI 3-kinase plays an important role in promoting smooth muscle proliferation in the vascular tree, i.e., vascular smooth muscle cells (Thyberg, 1998, European Journal of Cell Biology 76(1):33-42), and in the lungs (airway smooth muscle cells). Krymskaya et al., 1999, American Journal of Physiology 277:65-78. Excessive proliferation of vascular smooth muscle cells plays an important role in the formation of atherosclerotic plaques and in the development of neointimal hyperplasia following invasive vascular procedures. Scwartz et al., 1984, Progress in Cardiovascular Disease 26:355-372; Clowes et al., 1978, Laboratory Investigations 39:141-150. Moreover, excessive proliferation of airway smooth muscle cells leads to the development of COPD in the setting of asthma and chronic bronchitis. Inhibitors of PI 3-kinase therefore may be used to prevent vascular restenosis, atherosclerosis, and COPD.

PI 3-kinase also plays an important role in regulating tumor cells and in the propensity of these cells to undergo apoptosis growth. Sellers et al., 1999, The Journal of Clinical Investigation 104:1655-1661. Additionally, uncontrolled regulation of the PI 3-kinase lipid products PI(3,4,5)$P_3$ and PI(3,4)$P_2$ by the lipid phosphatase PTEN plays an important role in progression of a number of malignant tumors in humans. Leevers et al., 1999, Current Opinion in Cell Biology 11:219-225. Therefore, inhibitors of PI 3-kinase may be used to treat neoplasms in humans.

PI 3-kinase also plays an important role in leukocyte function (Fuller et al., 1999, The Journal of Immunology 162(11): 6337-6340; Eder et al., 1998, The Journal of Biological Chemistry 273(43):28025-31) and lymphocyte function (Vicente-Manzanares et al., 1999, The Journal of Immunology 163(7):4001-4012). For example, leukocyte adhesion to inflamed endothelium involves activation of endogenous leukocyte integrins by a PI 3-kinase-dependent signaling process. Furthermore, oxidative burst (Nishioka et al., 1998, FEBS Letters 441(1):63-66) and cytoskeletal reorganization (Kirsch et al., 1999, Proceedings National Academy of Sciences 96(11):6211-6216) in neutrophils appears to involve PI 3-kinase signaling. Thus, inhibitors of PI 3-kinase may be useful in reducing leukocyte adhesion and activation at sites of inflammation and therefore may be used to treat acute and/or chronic inflammatory disorders. PI 3-kinase also plays an important role in lymphocyte proliferation and activation. Fruman et al., 1999, Science 283 (5400):393-397. Given the important role of lymphocytes in auto-immune diseases, inhibitors of PI 3-kinase may be used in the treatment of such disorders.

The invention is further described by reference to the following examples, which are set forth by way of illustration only. Nothing in these examples should be taken as a limitation upon the overall scope of the invention.

EXAMPLE 1

Preparation of Morpholino-Substituted Pyridopyrimidine Derivatives

The morpholino-substituted pyridopyrimidine compounds of the present invention may be prepared using a common synthetic scheme, illustrated in this example, differing only in the starting 2-amino pyridine. Specifically, an appropriately substituted 2-amino pyridine is treated with diethylmalonate to yield a hydroxy-substituted pyridopyrimidine. The hydroxy-substituted pyridopyrimidine is subsequently reacted with phosphorus oxychloride to give a chloro-substituted pyridopyrimidine. Finally, the chloro-substituted pyridopyrimidine is reacted with morpholine to yield the morpholino-substituted pyridopyrimidine.

The present morpholino-substituted pyridopyrimidine derivatives were prepared according to the following general synthetic scheme:

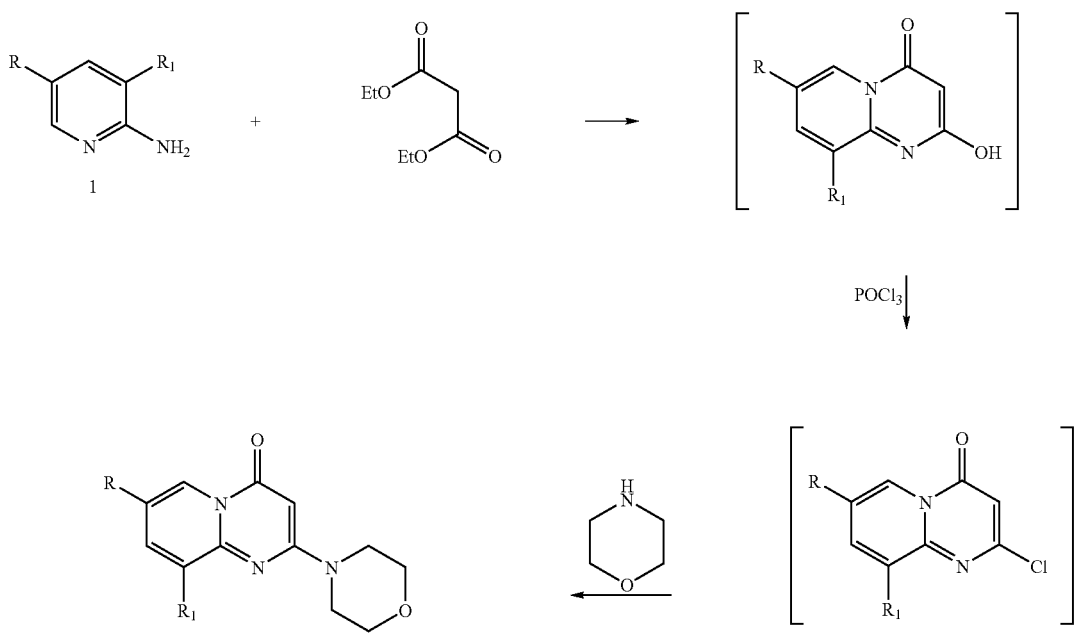

2. R = H, R₁ = CH₃ (TGX-25-A)
3. R = H, R₁ = Ph (TGX-37-A)
4. R = CH₃, R₁ = Ph (TGX-41-A)
5. R = H, R₁ = Benzyl (TGX-40-A)

The starting substituted 2-amino pyridine (compound 1) was 2-amino-3-methyl pyridine for TGX-25 (compound 2), 2-amino-3-phenyl pyridine for TGX-37 (compound 3), 2-amino-3-phenyl-5-methyl pyridine for TGX41 (compound 4), and 2-amino-3-benzyl pyridine for TGX-40 (compound 5).

2-amino-3-phenyl pyridine was prepared as follows: 3-phenyl pyridine (300 mg, 2 mmol) was dissolved in para-xylene (6 ml), and sodamide (84 mg, 2.1 mmol) was then added. The reaction mixture was heated to reflux temperature for 8 hours. The reaction mixture was cooled, poured onto ice/water (25 ml), and extracted with dichloromethane. The organic extracts were washed with water and brine, and dried over anhydrous sodium sulphate. The sodium sulphate was removed by filtration, and the filtrate was evaporated to dryness and recrystallized from a mixture of diethyl ether and petroleum ether to provide 2-amino-5-phenyl pyridine (95 mg). The mother liquors from the crystallization were evaporated to dryness and subjected to purification by column chromatography (silica), thereby eluting the solvent ethyl acetate:petroleum ether (30:70). The desired product, 2-amino-3-phenyl pyridine, was obtained as a fine yellow powder (15 mg).

2-amino-3-phenyl-5-methyl pyridine was prepared as follows: 2-amino-5-picoline (10.8 g, 0.1 M) was dissolved in glacial acetic acid (200 ml), and N-bromosuccinamide (20 g, 0.11 M) was added. The reaction mixture was stirred at room temperature for 17 hours. The reaction mixture was poured onto ice/water and the solid removed by filtration. The filtrate was basified with solid sodium hydroxide, and the resulting precipitate was isolated by filtration (12.8 g). The product, 2-amino-3-bromo-5-methylpyridine (3.7 g, 20 mmol), was dissolved in anhydrous DMSO (100 ml) under an atmosphere of nitrogen. Phenylboronic acid (2.66 g, 22 mmol) was added, followed by the addition of potassium carbonate (9.66 g, 70 mmol) and bis(triphenylphosphine)-palladium(II)chloride (426 mg, 0.6 mmol). The reaction mixture was heated to 80° C. with stirring for 15 hours. The reaction was cooled, poured into ice/water, and the crude product was collected by filtration. The resultant material was treated with 1 M aqueous hydrochloric acid (200 ml), stirred for 10 minutes, and filtered to remove insoluble residues. The filtrate was basified with solid sodium hydroxide, and the resultant yellow precipitate was filtered and dried to provide the product, 2-amino-3-phenyl-5-methyl pyridine, as a pale yellow solid (2.25 g).

2-amino-3-benzyl pyridine was prepared from 3-benzyl pyridine as described in Kelly et al., 1990, The Journal of the American Chemical Society 112:8024 (1990).

TGX-40 was prepared as follows: 2-amino-3-benzyl-pyridine (5.4 g) was treated with diethylmalonate (12 g) at 190-200° C. for 40 min. The excess of diethylmalonate was evaporated with a stream of nitrogen gas at the same temperature. The resulting solid was triturated three times with diethyl-ether and dried in vacuo (2.4 g, 28%). This hydroxypyrimidine derivative (528 mg) was then treated with an excess of POCl₃ (6 ml) and refluxed for 45 min. The reaction mixture was brought to room temperature and poured onto ice. The resulting precipitate was filtered and dried (341 mg, 59%). The crude chloroderivative (191 mg) was dissolved in ethanol (10 ml) containing morpholine (1 ml) and refluxed for 4 hrs. The reaction mixture was brought to room temperature and concentrated in vacuo. The residue was treated with aqueous bicarbonate and the resulting precipitate was then filtered and dried (151 mg, 78%).

TGX-101 was prepared as follows:

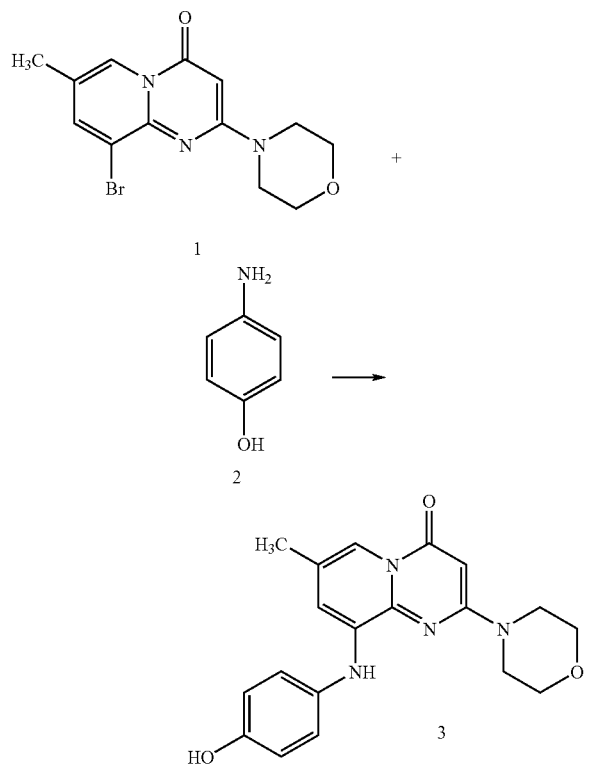

A mixture of a bromo derivative (compound 1) (324 mg, 1 mmol), 4-aminophenol (compound 2) (110 mg, 1 mmol), potassium t-butoxide (225 mg, 2 mmol), and PdCl$_2$ (dppf) (35 mg, 0.05 mmol) in THF was stirred at refluxing temperature for 20 hours over a nitrogen atmosphere. The reaction mixture was cooled and concentrated in vacuo. The resulting residue was diluted with water to give a dark green precipitate, which was filtered and dried. The solid was further purified by triturating with diethyl ether (two times) and dichloromethane (two times) successively, to give the required product (compound 3) (140 mg).

$^1$H NMR (300 MHz, DMSO) for TGX-101: δ 9.37(s, 1H, —OH), 7.96(s, 1H), 7.79(s, 1H, —NH), 7.13(d, J=8.7 Hz, 2H), 6.80(d, J=8.7 Hz, 2H), 6.66(d, J=1.8 Hz, 1H), 5.58 (s, 1H), 3.65(br s, 8H), 2.16(s, 3H).

By means of the above procedure, TGX-107 was prepared from the bromo derivative (compound 1) and 4-chloroaniline, TGX-108 was prepared by coupling compound 1 with 4-chlorobenzylamine, TGX-109 was prepared by coupling compound 1 with para-cresol, TGX-112 was prepared by coupling compound 1 with 4-pyridylamine, TGX-120 was prepared by coupling compound 1 with 4-aminopyridine. In a similar manner, TGX-123 and TGX-124 and TGX-126 and TGX-130 were prepared by coupling compound 1 with the appropriate substituted amine.

EXAMPLE 2

Preparation of 8-substituted 2-morpholinyl-4H-pyrido[1,2-a]pyrimidin-4-ones

8-Substituted 2-morpholinyl-4H-pyrido[1,2-a]pyrimidin-4-ones were prepared according to general procedure shown below. In brief, 8-benzyloxy-2-morpholinyl-4H-pyrido[1,2-a]pyrimidin-4-one (TGX-131) was debenzylated by treatment with trifluoromethane sulfonic anhydride and the resultant 8-hydroxy-2-morpholinyl-4H-pyrido[1,2-a]pyrimidin-4-one was derivatised by copper-promoted arylation using arylboronic acids adapting the method of Evans et al., 1998. Tetrahedron Lett. 39:2937-2940 (Example 2A) or base catalysed alkylation using arylmethyl halides (Example 2B).

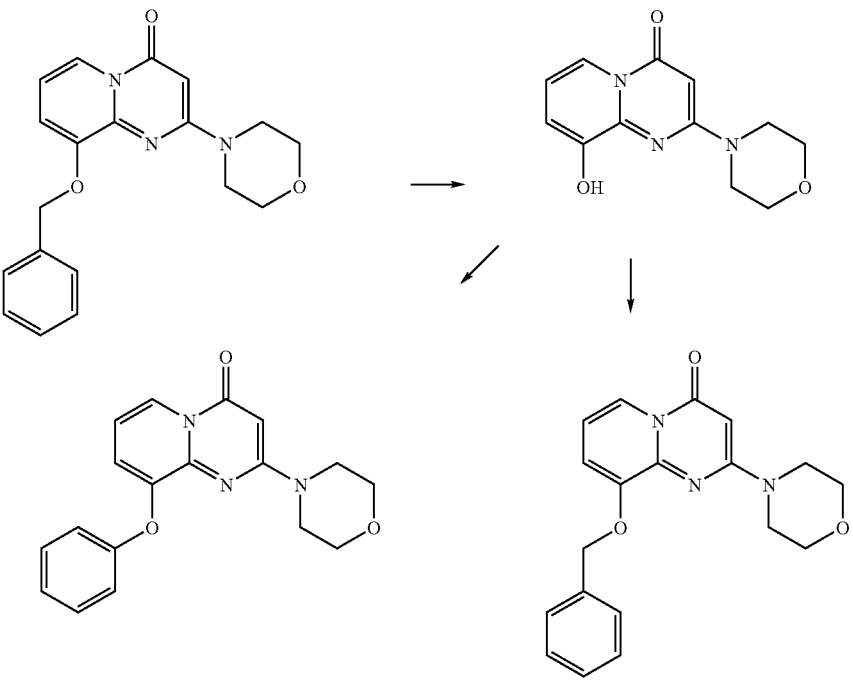

EXAMPLE 2A

2-Morpholinyl-8phenoxy-4H-pyrido-[1,2a]pyrimidin-4-one (TGX-141)

8Hydroxy-2-morpholinyl-4H-pyrido[1,2-a]pyrimidin-4-one

A solution of 8-benzyloxy-2-morpholinyl-4H-pyrido[1,2-a]pyrimidin-4-one (0.97 g, 2.9 mmol) in dichloromethane (50 ml) under nitrogen was treated dropwise with trifluoromethanesulfonic anhydride (1 ml, 6.0 mmol) and the mixture was stirred at RT overnight. Methanol (20 ml) was added and the solution stirred for a further 1 h, then the solution was evaporated to dryness. The residue was taken up in ethyl acetate, washed with brine, dried and then eluted through a silica column using a gradient of 0-5% methanol in ethyl acetate. The product was obtained as a brown powder (0.35 g)

2-Morpholinyl-8-phenoxy-4H-pyrido[1,2a]pyrimidin-4-one (TGX-141)

8-Hydroxy-2-morpholinyl-4H-pyrido[1,2-a]pyrimidin-4-one (0.2 g, 0.81 mmol), phenylboronic acid (0.29 g, 2.4 mmol), and copper acetate (0.20 g, 1.6 mmol) were suspended in dichloromethane and treated with triethylamine (0.23 ml, 1.6 mmol) and the mixture was stirred at RT for 4 days. The product was adsorbed onto silica and eluted through a silica column with ethyl acetate to yield a pale tan solid (0.026 g).

$^1$H-NMR (CDCl$_3$, 300 MHz): δ 3.45 (t, 4H, J=5 Hz), 3.63 (t, 4H, J=5 Hz), 5.59 (s, 1H), 6.8 (t, 1H, J=8 Hz), 7.40 (t, 2H, J=8.7 Hz), 7.45-7.55 (m, 3H), 8.18 (dd, 1H, J=9.0 Hz, 2 Hz).

In a similar manner but utilizing the appropriate arylboronic acid was also prepared:

8-(4-Fluoro-3-methylphenyl)oxy-4H-pyrido[1,2-a]pyrimidin-4-one (TGX-168) and 8-(2-methylphenyl)oxy-4H-pyrido[1,2-a]pyrimidin-4-one (TGX-182)

EXAMPLE 2B

8-(2-chlorophenyl)methoxy-2-morpholinyl-4H-pyrido[1,2-a]pyrimidin-4-one (TGX-177)

8-Hydroxy-2-morpholinyl-4H-pyrido[1,2-a]pyrimidin-4-one (59 mg, 0.24 mmol) was dissolved in acetonitrile (10 ml) and then treated with anhydrous potassium carbonate (197 mg, 1.4 mmol) followed by 2-chlorobenzylbromide (46 mg, 0.29 mmol) and the mixture was stirred at 80° C. overnight. Upon cooling the mixture was adsorbed directly onto silica, then eluted through a silica column using ethyl acetate. The purified product was obtained as a tan solid (34 mg).

$^1$H-NMR (CDCl$_3$, 300 MHz): δ 3.70 (t, 4H, J=5 Hz), 3.80 (t, 4H, J=5 Hz), 5.34 (s, 2H), 5.66 (s, 1H), 6.8 (t, 1H, J=8 Hz), 7.00 (d, 1H, J=8 Hz), 7.30 (m, 2H), 7.4 (m, 1H), 7.65 (m, 1H), 8.58 (d, 1H, J=8 Hz).

In a similar fashion but utilizing the appropriate arylmethyl halide were prepared:

8-(2-pyridinylmethyl)oxy-2-morpholinyl-4H-pyrido[1,2-a]pyrimidin-4-one (TGX-148);

8-(3-pyridinylmethyl)oxy-2-morpholinyl-4H-pyrido[1,2-a]pyrimidin-4-one (TGX-140);

8-(4-pyridinylmethyl)oxy-2-morpholinyl-4H-pyrido[1,2-a]pyrimidin-4-one (TGX-185);

8-(3-chlorophenyl)methoxy-2-morpholinyl-4H-pyrido[1,2-a]pyrimidin-4-one (TGX-176);

8-(4-bromophenyl)methoxy-2-morpholinyl-4H-pyrido[1,2-a]pyrimidin-4-one (TGX-175);

8-(4t-butylphenyl)methoxy-2-morpholinyl-4H-pyrido[1,2-a]pyrimidin-4-one (TGX-169); and 8-(3-methoxyphenyl)methoxy-2-morpholinyl-4H-pyrido[1,2-a]pyrimidin-4-one (TGX-163).

EXAMPLE 2C

6-methyl-8-phenylaminomethyl-2-morpholinyl-4H-pyrido[1,2]pyrimidin-4-one (TGX-183)

TGX-183 was synthesised according to the following scheme. The key reactions involved in this synthetic sequence are a palladium catalysed vinylation and one step cleavage of the alkene functionality to an aldehyde group.

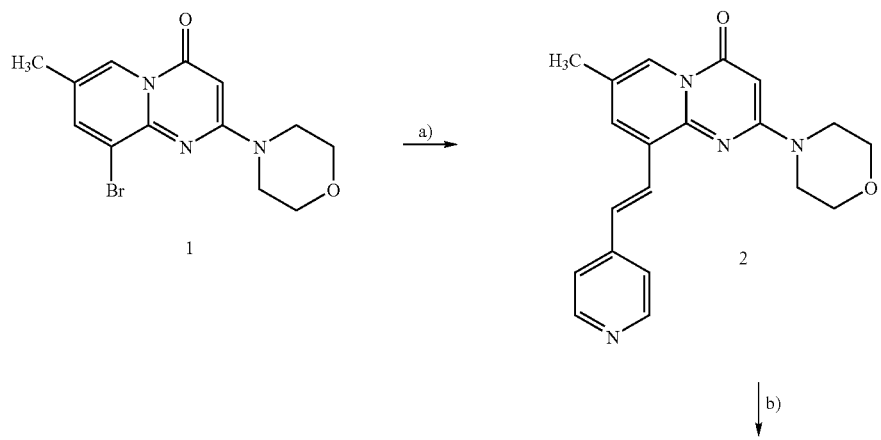

-continued

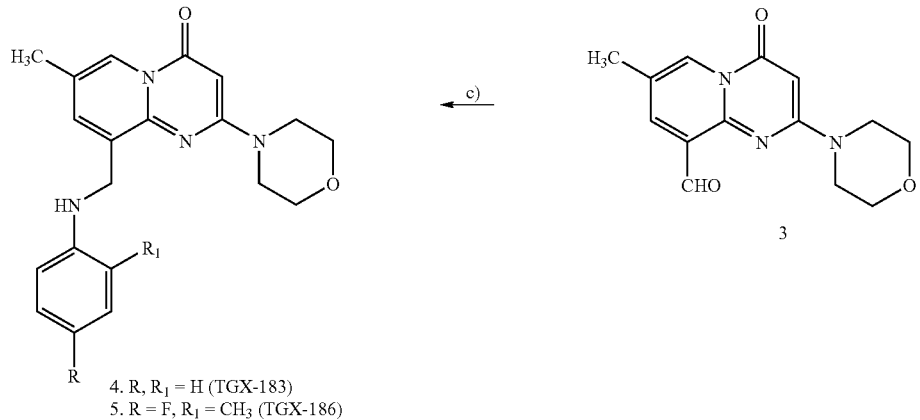

4. R, R₁ = H (TGX-183)
5. R = F, R₁ = CH₃ (TGX-186)

Reagents: a). 4-vinylpyridine, Cs₂CO₃, PdCl₂(dppf), DMF, 80° C., 16 hrs, b). CTAP, CH₂Cl₂, 2 hrs. RT c). i. NaBH₄, methanol, 0.5 hrs, RT, ii. methanesuphonyl chloride, Et₃N, CH₂Cl₂, 0° C. then aniline, reflux, 4 hrs.

The preparation of aldehyde 3 as follows:

A mixture of bromo compound 1 (324 mg, 1 mmol), 4-vinylpyridine (0.5 mL), CsCO₃ (0.98 g, 3 mmol), PdCl₂(dppf) (35 mg) in DMF (10 mL) was heated at 80° C. for 16 hours over a nitrogen atmosphere. The reaction mixture was brought to room temperature and poured onto ice. The resulting precipitate was filtered, dried in vacuo and taken to the next oxidation reaction without further purification. ¹H NMR (300 MHz, CDCl₃): δ 8.76 (s, 1H), 8.63 (d, J=4.73 Hz, 2H), 7.95 (d, J=16.63 Hz, 1H), 7.80 (d, J=1.98 Hz, 1H), 7.39 (d, J=6.10 Hz, 2H), 7.19 (d, J=16.48 Hz, 1H) 5.66 (s, 1H), 4.56 (s, 2H), 3.82 (m, 4H), 3.68 (m, 4H), 2.39 (s, 3H).

The crude product 2 obtained from the above reaction, was dissolved in dichloromethane (30 mL) to which was added cetyltrimethylammonium permanganate (Bhushan, V., et al *Synthesis*, 431, 1984) (0.5 g). The reaction mixture was stirred for 5 hours at room temperature. The reaction mixture was concentrated in vacuo to half of its original volume and adsorbed on silica gel. The required product 3 was isolated by short path column chromatography (silica gel, ethylacetate) as a yellow solid (158 mg, 58%). ¹H NMR (300 MHz, DMSO): δ 10.7 (s, 1H), 8.84 (s, 1H), 8.11 (s, 1H), 5.67 (s, 1H), 3.66 (br s, 8H), 2.35 (s, 3H).

The preparation of TGX-183 (4) as follows:

The yellow-coloured aldehyde 3 (158 mg) was suspended in methanol (5 mL) and reacted with sodium borohydride (20 mg) at room temperature. Stirring was continued until the reaction colour became white. The reaction mixture was concentrated in vacuo and diluted with water. The resulting white precipitate was filtered and dried to give the required product (150 mg) which was taken to next synthetic step without further purification. ¹H NMR (300 MHz, CDCl₃): δ 8.67 (s, 1H), 7.48 (s, 1H), 5.63 (s, 1H), 4.84 (br s, 2H), 3.80 (m, 4H), 3.60 (m, 4H), 2.34 (s, 3H).

The crude product (150 mg) which obtained from the previous reaction was suspended in dichloromethane (10 mL) to which was added triethylamine (0.14 mL, 1 mmol) followed by methanesulphonyl chloride (0.078 mL, 1 mmol) at ice-cold temperature. After 15 minutes, aniline(0.18 ml, 2 mmol) was added and refluxed for 4 hours. The reaction mixture was cooled and diluted with dichloromethane (50 ml). The dichloromethane layer was washed with water, brine and dried over sodium sulphate. After evaporation of the solvent in vacuo, the residue was purified by column chromatography (silica gel, ethyl acetate) to give the pure aniline derivative 4 (TGX-183) (120 mg). ¹H NMR (300 MHz, CDCl₃): δ 8.65 (s, 1H), 7.52 (s, 1H), 7.18 (m, 2H), 6.74 (br t, 1H), 6.61 (br d, 2H), 5.64 (s, 1H), 4.56 (s, 2H), 3.79 (m, 4H), 3.63 (m, 4H), 2.28 (s, 3H).

TGX-183:

¹H NMR (300 MHz, DMSO): δ 8.52 (s, 1H), 7.52 (s, 1H), 7.06 (d, J=7.0 Hz, 1H), 7.03 (d, J=7.0 Hz, 1H), 6.55-6.50 (m, 3H), 6.20 (t, J=5.8 Hz, 1H, —NH), 5.62 (s, 1H), 4.44 (d, J=5.8 Hz, 2H), 3.66-3.59 (m, 8H), 2.23 (s, 3H).

6-methyl-8-(2-methyl-4-fluorophenyl)aminomethyl-2-morpholinyl-4H-pyrido[1,2-a]pyrimidin-4-one (TGX-186) (5) was prepared according to the procedure described for TGX-183 (4) except 4-fluoro-2-methylaniline was used instead of aniline during the last step of the synthetic sequence.

¹H NMR (300 MHz, DMSO): δ 8.52 (s, 1H), 7.47 (s, 1H), 6.87 (dd, J=9.5, 3.0 Hz, 1H), 6.72 (m, 1H), 6.23 (dd, J=9.0, 4.9 Hz, 1H), 5.63 (s, 1H), 5.52 (t, J=5.8 Hz, 1H, —NH), 4.49 (d, J=6.1 Hz, 2H), 3.67-3.60 (m, 8H), 2.23 (s, 3H), 2.17 (s, 3H).

EXAMPLE 3

Preparation of Morpholino-Substituted Quinolone Derivatives

The morpholino-substituted quinolone compounds of the present invention were prepared according to the following general synthetic scheme:

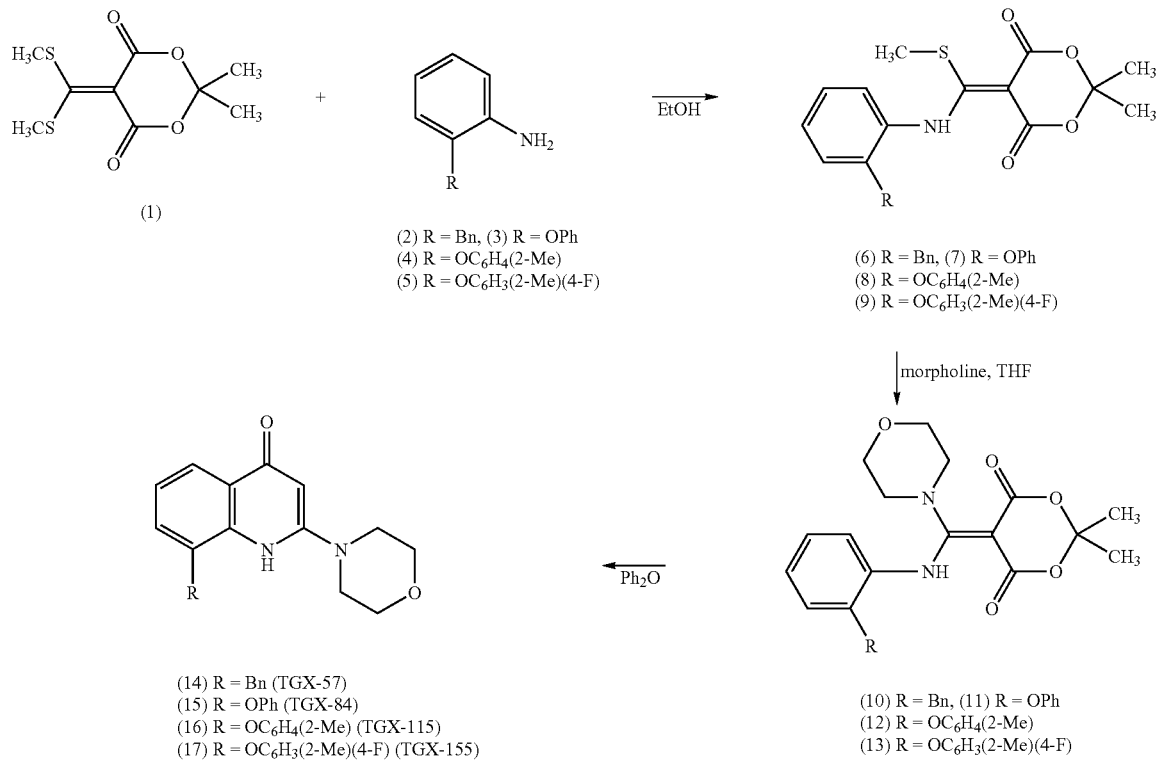

(14) R = Bn (TGX-57)
(15) R = OPh (TGX-84)
(16) R = OC₆H₄(2-Me) (TGX-115)
(17) R = OC₆H₃(2-Me)(4-F) (TGX-155)

TGX-57 (compound 14), TGX-84 (compound 15), TGX-115 (compound 16) and TGX-155 (compound 17) were prepared by adapting the procedure of Huang et al., 1989, Synthesis 317, starting with the appropriately substituted aniline and Meldrum's acid derivative (compound 1) (Huang et al., 1986, Synthesis 967). Anilines (compound 4) and (compound 5) in turn were synthesized by reaction of 2-chloronitrobenzene with o-cresol or 4-fluoro-o-cresol to yield the corresponding nitro compounds followed by Pd catalyzed hydrogenation.

Substitution of Meldrum's acid derivative (compound 1) with 2-benzylaniline (compound 2) (or 2-phenoxyanilines, compounds 3-5) yielded intermediate compound 6 (or compounds 7-9) which after reaction with morpholine resulted in compound 10 (or compounds 11-13). Finally, the required quinolinone skeleton was constructed by refluxing compound 10 (or compounds 11-13) in diphenyl ether for 15 minutes.

Anilines (compounds 4 and 5) were prepared as follows: A mixture of 2-Chloronitrobenzene (5.68 g, 36 mmol), o-cresol (or 4-fluoro-o-cresol) (40 mmol) and potassium carbonate (14.9 g, 108 mmol) in DMSO (120 mL) was stirred at 80° C. for 18 h. Water (60 mL) was added and the reaction mixture extracted with ethyl acetate (3×200 mL). The combined organic extracts were sequentially washed with 1M sodium hydroxide (3×100 mL) and aqueous sodium chloride (100 mL), dried (sodium sulphate) and evaporated under reduced pressure to yield the corresponding nitrocompounds (95-100%). Pd/C catalysed hydrogenation of nitrocompounds in ethanol at ambient temperature for 7 h yielded the required anilines. The catalyst was filtered and the resultant filtrate evaporated under reduced pressure to yield aniline (compound 4) (or compound 5) as a brown oil (90-95%). The crude anilines (compounds 4-5) were used without further purification in the subsequent reaction with Meldrum's acid derivative (compound 1).

5-[Anilino(methylthio)methylene]-2,2-dimethyl-4,6-dioxo-1,3-dioxanes (compounds 6-9) were prepared as follows: A mixture of 5-[bis(methylthio)methylene]-2,2-dimethyl-4,6-dioxo-1,3-dioxane (compound 1) (2.48 g, 10 mmol), 2-substituted aniline (compound 2) (or compounds 3-5) (10 mmol) in ethanol (25 mL) was heated at 140° C. for 4.5 h. Evaporation of the solvent under reduced pressure yielded a crude yellow oil which, after purification by flash chromatography, using petroleum ether/ethyl acetate (9:1 and then 3:1) as eluent, yielded compound 6 (or compounds 7-9) (68-77%).

$^1$H NMR (300 MHz; CDCl$_3$) for 5-[2-benzylanilino(methylthio)methylene]-2,2-dimethyl-4,6-dioxo-1,3-dioxane (compound 6): δ 1.73 (6H, S, CH$_3$), 1.89 (3H, s, CH$_3$), 4.04 (2H, s, CH$_2$), 7.08-7.41 (9H, m, CHAr). $^1$H NMR (300 MHz; CDCl$_3$) for 5-[Methylthio-(2-phenoxyanilino)methylene]-2,2-dimethyl-4,6-dioxo-1,3-dioxane (compound 7): $^1$H NMR (300 MHz; CDCl$_3$): δ 1.62 (6H, s, CH$_3$), 2.20 (3H, s, CH$_3$), 6.90-7.72 (9H, m, CHAr). $^1$H NMR (300 MHz; CDCl$_3$) for 5-[2-(2'-Methylphenoxy)anilino(methylthio)-methylene]-2,2-dimethyl-4,6-dioxo-1,3-dioxane (compound 8): δ 1.70 (6H, s, CH$_3$), 2.25 (3H, s, CH$_3$), 2.31 (3H, s, CH$_3$), 6.80-7.44 (8H, m, CHAr). $^1$H NMR (300 MHz; CDCl$_3$) for 5-[2-(4'-Fluoro-2'-methylphenoxy)anilino(methylthio)methylene]-2,2-dimethyl-4,6-dioxo-1,3-dioxane (compound 9): δ 1.72 (6H, s, CH$_3$), 2.22 (3H, s, CH$_3$), 2.33 (3H, s, CH$_3$), 6.72-7.44 (7H, m, CHAr), 7.8 (1H, s, NH).

5-[Anilino(morpholino)methylene]-2,2-dimethyl-4,6-dioxo-1,3-dioxanes (compounds 10-13) were prepared as follows: A mixture of 5-[anilino(methylthio)-methylene]-2,2-dimethyl-4,6-dioxo-1,3-dioxane (compound 6) (or compounds 7-9) (18 mmol) and morpholine (3.15 mL, 36 mmol) in tetrahydrofuran (100 mL) was heated at reflux temperature overnight. The solvent was evaporated and the crude yellow solid was washed with ether to yield compound 10 (or compounds 11-13) (90-95%) as a white solid. $^1$H NMR (300 MHz; CDCl$_3$) for 5-[2-Benzylanilino(morpholino)methylene]-2,2-dimethyl-4,6-dioxo-1,3-dioxane (compound 10): δ 2.04 (6H, s, CH$_3$), 3.39 (4H, t, J4.9 Hz, CH$_2$), 3.70 (4H, t, J4.9 Hz, CH$_2$), 6.55 (1H, d, J7.5 Hz, CHAr), 6.95 (1H, td, J7.5, 1.2 Hz, CHAr), 7.08-7.23 (7H, m, CHAr). $^1$H NMR (300 MHz; CDCl$_3$) for 5-[Morpholino-(2-phenoxyanilino)methylene]-2,2-dimethyl-4,6-dioxo-1,3-dioxane (compound 11): δ 1.60 (6H, s, CH$_3$), 3.31 (4H, t, J4.7 Hz, CH$_2$), 3.71 (4H, t, J4.7 Hz, CH$_2$), 6.92-7.35 (9H, m, CHAr). $^1$H NMR (300 MHz; CDCl$_3$) for 5-[2-(2'-Methylphenoxy)anilino(morpholino)-methylene]-2,2-dimethyl-4,6-dioxo-1,3-dioxane (compound 12): δ 1.67 (6H, s, CH$_3$), 2.19 (3H, s, CH$_3$), 3.32 (4H, t, J4.6 Hz, CH$_2$), 3.74 (4H, t, J4.6 Hz, CH$_2$), 6.73 (1H, dd, J 8.0, 1.5 Hz, CHAr), 6.90 (1H, dd, J8.0, 1.5 Hz, CHAr), 7.08-7.24 (6H, m, CHAr), 9.51 (1H, s, NH). $^1$H NMR (400 MHz; CDCl$_3$) for 5-[2-(4'-Fluoro-2'-methylphenoxy)anilino-(morpholino)methylene]-2,2-dimethyl-4,6-dioxo-1,3-dioxane (compound 13): δ 1.68 (6H, s, CH$_3$), 2.17 (3H, s, CH$_3$), 3.33 (4H, t, J4.6 Hz, CH$_2$), 3.74 (4H, t, J4.6 Hz, CH$_2$), 6.66 (1H, dd, J8.0, 1.2 Hz, CHAr), 6.89-7.29 (5H, m, CHAr), 7.41 (1H, t, J8.0 Hz, CHAr), 9.47 (1H, s, NH).

2-Morpholino-4-quinolones (compound 14-17; TGX-57, TGX-84, TGX-115 and TGX-155) were prepared as follows: 5-[Anilino(morpholino)methylene]-2,2-dimethyl-4,6-dioxo-1,3-dioxane (compound 10) (or compounds 11-13) was heated in diphenyl ether (3-4 mL) at 240° C. for 15 minutes. The reaction mixture was cooled to room temperature and petroleum ether (bp 60-90° C., 30 mL) added to yield the crude compound which after purification by flash chromatography, using petroleum ether/ethyl acetate (1:1) and then ethyl acetate/methanol (9:1) as eluent, yielded compound 14 (or compounds 14-17) (40-50%). $^1$H NMR (400 MHz; CDCl$_3$) for 8-Benzyl-2-morpholinoquinolone (compound 14; TGX-57): δ 3.11 (4H, t, J4.6 Hz, CH$_2$), 3.58 (4H, t, J4.6 Hz, CH$_2$), 4.44 (2H, s, CH$_2$), 6.75 (1H, s, CH), 7.21-7.33 (6H, m, CHAr), 7.59 (1H, d, J7.3 Hz, CHAr), 7.78 (1H, d, J7.3 Hz, CHAr). $^1$H NMR (400 MHz; CDCl$_3$) for 2-Morpholino-8-phenoxy-4-quinolone (compound 15; TGX-84): δ 3.30 (4H, t, J5 Hz, CH$_2$), 3.82 (4H, br.s, CH$_2$), 5.80 (1H, s, CH), 6.98 (1H, d, J7.5 Hz, CHAr), 7.09 (2H, d, J8.0 Hz, CHAr), 7.13 (1H, t, J8.0 Hz, CHAr), 7.20 (1H, t, J7.5 Hz, CHAr), 7.40 (2H, t, J8.0 Hz, CHAr), 7.98 (1H, dd, J7.5, 1.2 Hz, CHAr). $^1$H NMR (300 MHz; CDCl$_3$) for 8-(2'-Methylphenoxy)-2-morpholino-4-quinoline (compound 16; TGX 115): δ 2.24 (3H, S, CH$_3$), 3.33 (4H, t, J4.8 Hz, CH$_2$), 3.87 (4H, t, J4.8 Hz, CH$_2$), 5.80 (1H, s, CH), 7.01 (1H, d, J8.1 Hz, CHAr), 7.08 (1H, t, J8.0 Hz, CHAr), 7.16-7.29 (3H, m, CHAr), 7.32 (1H, d, J8.0 Hz, CHAr), 7.92 (1H, d, J 8.0 Hz, CHAr), 8.26 (1H, s, NH). $^1$H NMR (300 MHz; CDCl$_3$) for 8-(4'-Fluoro-2'-methylphenoxy)-2-morpholino-4-quinolone (compound 17; TGX 155): δ 2.20 (3H, s, CH$_3$), 3.35 (4H, t, J4.8 Hz, CH$_2$), 3.88 (4H, t, J4.8 Hz, CH$_2$), 5.80 (1H, s, CH), 6.65 (1H, J 8.1 Hz, CHAr), 6.95-7.10 (4H, m, CHAr), 7.92 (1H, d, J8.1 Hz, CHAr), 8.23 (1H, s, NH).

With the appropriately 2-substituted aniline and with coupling with the Meldrum's acid derivative (compound 3), TGX-99, TGX-106, TGX-111, TGX-113, and TGX-121 were prepared as outlined above.

EXAMPLE 4

Preparation of Morpholino-Substituted Benzopyranone Derivatives 8-(Substituted)-2-(4-morpholinyl)-4H-1-benzopyran-4-ones were prepared according to the following general procedure adapted from Morris et al., 1994, Synth. Commun, 24: 849-858. In brief, the lithium enolate of acetyl morpholine is reacted with a substituted salicylate ester (1) to yield an intermediate salicylacetamide (2). Cyclodehydration of (2) with trifluoromethanesulfonic anhydride yields the substituted morpholino substituted-benzopyranone (3).

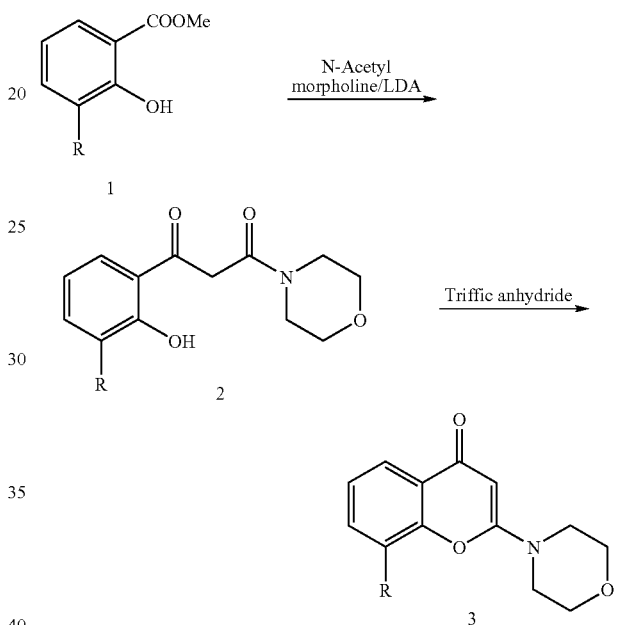

Specific substituents in the 8-position of the product (3) were introduced either into the precursor (1) (Method A) or by elaboration of 2-(4-morpholinyl)-8-trifluoromethanesulfonyloxy-4H-1-benzopyran-4-one (3, R=CF$_3$SO$_3$) (Methods B and C).

Method A

EXAMPLE A-1

2-morpholinyl-8-phenylmethyl)-4H-1-benzopyran-4-one (TGX-90) 3-(phenylmethyl)salicylaldehyde To a warm, stirred mixture of sodium hydroxide (8.0 g) in water (8.0 ml) was added a warmed solution of 2-hydroxydiphenylmethane (1), (4.9 g, 27 mmol) in ethanol (4 ml) and the mixture heated to 65° C. Chloroform (4.1 ml) was added down a water condenser and the resulting mixture began to reflux. After 1 h at reflux, the mixture was cooled in ice, acidified to pH 2 with 1N HCl and extracted with ethyl acetate (3×30 ml). The combined extracts were dried (Na$_2$SO$_4$) and the solvent removed to yield a dark brown gum. The product was eluted through a silica column, using 0-10% ethyl acetate in petroleum spirit to yield a yellow oil (1.33 g, 24%)

Methyl 3-(phenylmethyl)salicylate

According to the general method of Sharma et al., 2000, Synth. Commun., 30:397-405, a stirred solution of the 3-(phenylmethyl)salicylaldehyde (1.27 g, 6 mmol) in ethanol (16 ml) was treated dropwise with a solution of silver nitrate (2.0 g, 12 mmol) in water (16 ml). A solution of potassium hydroxide (2.69 g, 48 mmol) was then added dropwise over 40 minutes. The solution was allowed to stir at RT for 6 h. The mixture was filtered through a pad of celite, and the filter pad washed with water (2×10 ml). The filtrate was washed with diethyl ether (2×15 ml) and then acidified with 1N HCl. The milky suspension was extracted with diethyl ether (2×30 ml), and the combined extracts were dried ($Na_2SO_4$) and the solvent removed to yield 3-(phenylmethyl)salicylic acid as a tan solid (0.47 g, 34%). $^1$H-NMR ($CDCl_3$, 400 MHz): δ 4.02 (s, 2H), 6.84 (t, 1H, J=8 Hz), 7.19-7.32 (m, 6H), 7.79 (d, 1H, J=8 Hz), 10.74 (s, 1H).

To a solution of the acid (0.47 g, 2.1 mmol) in dry methanol (40 ml) was added conc. Sulfuric acid (0.47 g) and the solution heated to reflux for 96 h. Upon cooling the the methanol was removed and the residue taken up in water (50 ml), and extracted with dichloromethane (3×30 ml). The combined extracts were dried ($Na_2SO_4$), and the solvent removed. The residue was eluted through a silica column using 5% ethyl acetate in petroleum spirit to yield a colorless oil (0.23 g, 46%). $^1$H-NMR ($CDCl_3$, 300 MHz): δ 3.94 (s, 3H), 4.03 (s, 2H), 6.81 (t, 1H, J=8 Hz), 7.20-7.32 (m, 6H), 7.73 (dd 1H, J=8 Hz, 1.5 Hz), 11.10 (s, 1H).

(4-Morpholinyl)-3-[2'-hydroxy-3'-(phenylmethyl) phenyl]-3-oxopropanamide

A cooled solution of diisopropylamine (0.62 ml, 4.4 mmol) in tetrahydrofuran (10 ml) was treated with n-butyl lithium in hexane (1.6 M, 2.73 ml, 4.4 mmol) and the solution stirred for 10 minutes at 0° C. 4-Acetylmorpholine (0.25 ml, 2.2 mmol) was added and stirring was continued at 0° C. for a further 30 minutes. Methyl 3-(phenylmethyl)salicylate (0.33 g, 1.4 mmol) in tetrahydrofuran was added dropwise and the mixture allowed to come to RT and stirring was continued overnight. The solution was neutralised with 1N HCl, and the mixture extracted with dichloromethane (3×30 ml). The combined extracts were dried ($Na_2SO_4$) and the solvent removed. The residue was eluted through a silica column with 0-10% methanol in dichloromethane to yield a pale yellow oil (0.55 g), which contained residual 4-acetylmorpholine. The product was not further purified but reacted as follows.

2-morpholinyl-8-(phenylmethyl)-4H-1-benzopyran-4-one (TGX-90)

To a stirred solution of the partially purified (4-morpholinyl)-3-[2'-hydroxy-3'-(phenylmethyl)phenyl]-3-oxopropanamide (0.55 g) in dichloromethane under nitrogen was added dropwise trifluoromethanesulfonic anhydride and the solution was stirred at RT overnight. The solvent was removed, and the residue taken up in methanol (10 ml) and stirring continued for a further 4 h. The methanol was removed and the residue treated with half saturated sodium bicarbonate solution (30 ml), and extracted with dichloromethane (3×20 ml). The combined extracts were washed (sat. NaCl), dried ($Na_2SO_4$) and the solvent removed to yield an orange solid, which was recrystallized from ethyl acetate to yield pale pink, fine needles (0.12 g, 27% from 3).

$^1$H-NMR ($CDCl_3$, 300 MHz): δ 3.32 (t, 3H), 3.69 (t, 3H), 4.19 (s, 2H), 5.47 (s, 1H), 7.13 (d, 1H, J=8 Hz), 7.20-7.40 (m, 6H), 8.08 (dd 1H, J=8 Hz, 1.8 Hz).

EXAMPLE A-2

2-(4-morpholinyl)-8-phenoxy-4H-1-benzopyran-4-one (TGX-134) Metal 2,3-dihydroxybenzoate A mixture of 2,3-dihydroxybenzoic acid (3.8 g, 24.6 mmol) in methanol (300 ml) was treated dropwise with conc. Sulfuric acid (4.2 g) and the resultant solution was heated at reflux temperature overnight. Upon cooling the solvent was evaporated and the residue poured into ice-water. The mixture was extracted with dichloromethane (3×50 ml) and the combined organic fractions dried ($Na_2SO_4$) and concentrated to yield a pale tan solid (4.05 g).

$^1$H-NMR ($CDCl_3$, 400 MHz): δ 3.92 (s, 3H), 6.76 (t, 1H, J=7.6 Hz), 7.08 (d, 1H, J=7.2 Hz), 7.33 (d, 1H, J=7.6 Hz), 10.88 (s, 1H).

Methyl 3-phenoxy-2-hydroxybenzoate

To a mixture of methyl 2,3-dihydroxybenzoate (1.50 g, 8.9 mmol), phenylboronic acid (1.08 g, 8.9 mmol) and copper acetate (1.62 g, 8.9 mmol) suspended in dichloromethane (100 ml) was added triethylamine (6.15 ml, 44.5 mmol) and the mixture was stirred at room temperature for 96 h. The solvent was removed and the product chromatographed through a silica column using a gradient of 0-10% methanol in dichloromethane. The product was obtained as a pale yellow oil (0.25 g).

$^1$H-NMR ($CDCl_3$, 300 MHz): δ 3.97 (s, 3H), 6.86 (t, 1H, J=8 Hz), 6.9-7.4 (m, 6H), 7.67 (dd, 1H, J=8 Hz, 2 Hz), 10.94 (s, 1H).

2-(4morpholinyl)-8-phenoxy-4H-1-benzopyran-4one (TGX-134)

Condensation of the lithium enolate of N-acetyl morpholine (0.21 g, 1.6 mmol) with methyl 3-phenoxy-2-hydroxybenzoate (0.25 g, 1.0 mmol) followed by cyclodehydration with trifluoromethanesulfonic anhydride (0.60 ml, 3.6 mmol) as described above yielded TGX-134 as an off-white solid (0.090 g).

$^1$H-NMR ($CDCl_3$, 300 MHz): 3.22 (t, 4H, 6 Hz), 3.63 (t, 4H, 6 Hz), 5.46 (s, 1H), 6.97 (d, 2H, J=9 Hz), 7.09 (t, 1H, J=8 Hz), 7.2-7.4 (m, 4H), 7.94 (dd, 1H, J=6 Hz, 4 Hz)

EXAMPLE A-3

2-(4-morpholinyl)-8-trifluoromethanesulflonyloxy-4H-1-benzopyran-4-one

Methyl 2-hydroxy-3-trifluoromethanesulfonyloxy-benzoate

To methyl 2,3-dihydroxybenzoate (2.1 g, 12.5 mmol) dissolved in dichloromethane (50 mL) was added pyridine (2.0 ml, 25 mmol) and dimethylaminopyridine (150 mg, 1.25 mmol). The mixture was cooled to 0° C. and trifluoromethane sulfonic anhydride was added dropwise by syringe. The ice bath was removed and stirred at room temperature for 60 h. The organic layer was washed twice with 1 M HCl (20 ml), dried ($Na_2SO_4$) and concentrated to dryness in vacuo. The solid was recrystallized from ethyl acetate to yield colourless crystals (2.5 g).

$^1$H-NMR (CDCl$_3$, 300 MHz): δ 3.99 (s, 3H), 6.93 (t, 1H, J=8.1 Hz), 7.43 (d, 1H, J=8.4 Hz), 7.86 (d, 1H, J=8.1 Hz), 11.2 (s, 1H).

2-(4morpholinyl)-8-trifluoromethanesulfonyloxy-4H-1-benzopyran-4-one

Condensation of the lithium enolate of N-acetyl morpoline (2.2 ml) with methyl 2-hydroxy-3-trifluoromethanesulfonyloxy-benzoate (3.56 g, 11.9 mmol) yielded the salicylacatamide (3.6 g). Cyclodehydration of the product with trifluormethanesulfonic anhydride (5.5 ml) as described above yielded the product as a colourless solid (1.21 g).

$^1$H-NMR (CDCl$_3$, 400 MHz): δ 3.57 (bs, 4H), 3.84 (bs, 4H), 5.52 (s, 1H), 7.38 (t, 1H, J=6.8 Hz), 7.48 (d, 1H, J=8.0 Hz), 8.15 (d, 1H, J=8.0 Hz).

Method B

EXAMPLE 1-B 2-(4-morpholinyl)-8-(4fluoro-2-methylphenyl)oxy-4H-1-benzopyran-4-one (TGX-184)

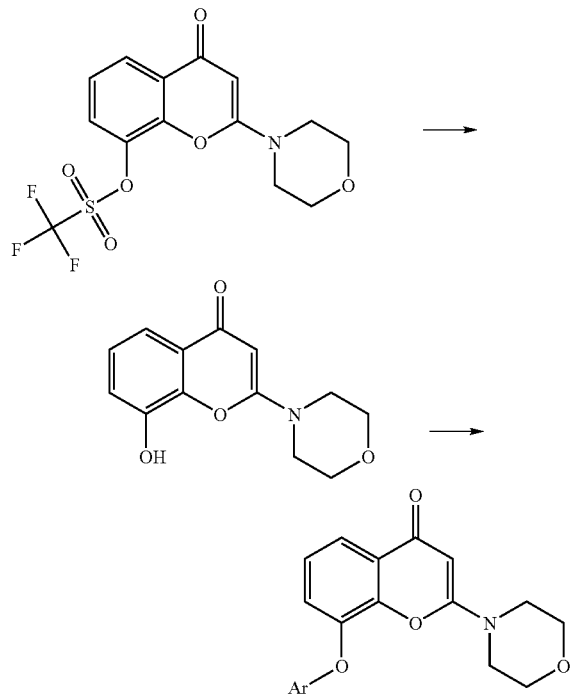

2-(4morpholinyl)-8-hydroxy-4H-1-benzopyran-4-one

To a solution of the trifluoromethanesulfonate ester (0.53 g, 1.4 mmol) in THF (25 ml) was added sodium t-butoxide (0.203 g, 2.1 mmol) and the mixture stirred at room temperature overnight. The solvent was removed and the residue was directly chromatographed through a column of silica, eluting with 0-10% methanol in dichloromethane to yield a white solid (0.19 g).

$^1$H-NMR (d$_6$-DMSO, 400 MHz): δ 3.49 (s, 4H), 3.69 (s, 4H), 5.45 (s, 1H), 7.10 (d, 2H, J=6.8 Hz), 7.31 (s, 1H), 10.14 (s, 1H).

2-(4morpholinyl)-8-(4-fluoro-2-methylphenyl)oxy-4H-1-benzopyran-4-one (TGX-184)

To a mixture of 2-(4-morpholinyl)-8-hydroxy-4H-1-benzopyran-4-one (77 mg, 0.31 mmol), 4-fluoro-2-methylphenylboronic acid (48 mg, 0.31 mmol) and copper acetate (57 mg, 0.31 mmol) suspended in dichloromethane (3.1 ml) was added triethylamine (216 uL, 1.56 mmol) and the mixture was stirred at room temperature for 24 h. The solvent was removed and the product chromatographed through a silica column with 0-10% methanol in dichloromethane to yield an off white solid (37 mg).

$^1$H-NMR (d$_6$-DMSO 300 MHz): δ 2.27 (s, 3H); 3.38 (t, 4H, 5 Hz), 3.74 (t, 4H, 5 Hz), 5.51 (s, 1H), 6.7-6.9 (m, 2H), 7.01 (m, 2H), 7.22 (t, 1H, J=9 Hz), 8.55 (dd, 1H, J=9Hz, 2 Hz).

In a similar manner were also synthesized:
8-phenoxy-2-morpholinyl-4H-1-benzopyran-4-one (TGX-134);
8-(2-methylphenyl)oxy-2-morpholinyl-4H-1-benzopyran-4-one (TGX-182); and
8-(4-fluoro-3-methylphenyl)oxy-2-morpholinyl-4H-1-benzopyran-4-one (TGX-173).

Method C

EXAMPLE C-1

2-morpholinyl-8-(4-fluorophenyl)-4H-1-benzopyran-4-one (TGX-165)

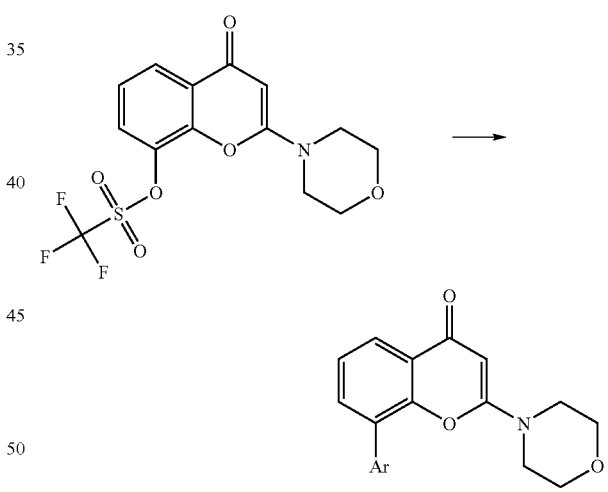

To a solution of the triflate (0.20 g, 0.52 mmol), potassium carbonate (0.182 g, 1.38 mmol) in acetonitrile (10 ml) bubbling under nitrogen, was added 4-fluorophenyl boronic acid (0.089 g, 0.63 mmol) followed by palladium acetate (0.012 g, 0.05 mmol) and the solution was heated under nitrogen for 24 h. Upon cooling the mixture was filtered and the filter cake washed with acetonitrile (10 ml). The filtrate and washings were combined and the solvent removed to yield a yellow solid which was was eluted through a silica column using ethyl acetate yielding a colourless solid (0.057 g).

$^1$H-NMR (CDCl$_3$, 300 MHz): δ 3.33 (t, 4H, J=5.3 Hz), 3.74 (t, 4H, J=5.3 Hz), 5.52 (s, 1H), 7.16 (t, 1H, J=10 Hz), 7.40 (t, 2H, J=8.7 Hz), 7.45-7.55 (m, 3H), 8.18 (dd, 1H, J=9.0 Hz, 2 Hz).

In this manner but utilizing the appropriate arylboronic acid and trifluoromethanesulfonate ester were prepared:
2-morpholinyl-8-(2-methylphenyl)-4H-1-benzopyran-4-one (TGX-145);
2-morpholinyl-8-(2-trifluoromethylphenyl)-4H-1benzopyran-4-one (TGX-135);
2-morpholinyl-8-(2-chlorophenyl)-4H-1-benzopyran-4-one (TGX-146); and
2-morpholinyl-8-(4-phenoxyphenyl)-4H-1-benzopyran-4-one (TGX-166).

EXAMPLE 5

In Vitro PI 3-Kinase Assay

The effect of TGX-25, TGX-33, TGX-37, TGX-40, TGX-41, TGX-57, TGX-84, TGX-90, TGX-93, TGX-98, TGX-99, TGX-101, TGX-106, TGX-107, TGX-108, TGX-109, TGX-111, TGX-112, TGX-113, TGX-115, TGX-120, TGX-121, TGX-123, TGX-124, TGX-126, TGX-127, TGX-130 or TGX-131on PI 3-kinase activity was determined using an in vitro PI 3-kinase assay. This assay was performed using PI 3-kinase immunoprecipitated from human platelets as the enzyme and PI as the substrate. The PI 3-kinase activity was quantitated by measuring the enzymatic incorporation of [$^{32}$P] into PI, forming PI([$^{32}$P]-3)P, as previously described (Susa et al., 1992, The Journal of Biological Chemistry 267 (32):22951-22956.

Washed human platelets were lysed in Triton X-100 lysis buffer (10 mM Tris, pH 7.4, 1% Triton X-100, 2 mM EDTA, 1 mM PMSF) for 30 minutes. The Triton X-100 insoluble fraction was removed by centrifugation of the cell lysates at 15,000 g for 10 minutes. PI 3-kinase was immunoprecipitated by mixing 500 µg of the cell lysate with 1 µg of a rabbit anti-rat antibody against the p85/110 form of PI 3-kinase and 30 µl of 50% Protein A-sepharose beads for 2 hours at 4° C. The Protein A-sepharose-bound PI 3-kinase was isolated by pelleting the beads at 15,000 g for 5 seconds, and washing three times with ice-old Triton X-100 lysis buffer followed by four washes with PI 3-kinase assay buffer (20 mM HEPES, pH 7.4, 1 mM EGTA, 5 mM MgCl$_2$).

PI stored in CHCl$_3$ was dried under N$_2$, resuspended in the lipid buffer (50 mM HEPES, pH 7.2, 1 mM EDTA) at a final concentration of 330 µg/ml, and sonicated for 6 minutes on ice. PI([$^{32}$P]-3)P was generated by mixing the immunoprecipitated PI 3-kinase for 20 minutes with 40 µl of the PI, 10 µl of ATP (1 mM) and $^{32}$P-r-ATP (0.5 µCi, 1 µCi/nmol), 10 µl of 10× kinase buffer, in a final assay volume of 100 µl adjusted with H$_2$O. TGX-25, TGX-33, TGX-37, TGX-40, TGX-41, TGX-57, TGX-84, TGX-90, TGX-93, TGX-98, TGX-99, TGX-101, TGX-106, TGX-107, TGX-108, TGX-109, TGX-111, TGX-112, TGX-113, TGX-115, TGX-120, TGX-121, TGX-123, TGX-124, TGX-126, TGX-127, TGX-130 or TGX-131 was preincubated with the PI 3-kinase for 5 minutes prior to the addition of ATP. The assay was terminated with 100 µl of 1 N HCl, and the PI([$^{32}$P]-3)P product extracted with 200 µl chloroform:methanol (1:1) and 500 µl 2 M KCl. The PI([$^{32}$P]-3)P in the chloroform phase was resolved by thin layer chromatography using a solvent system containing CHCl$_3$:MeOH:HAC:H$_2$O (43:38:5:7) (v:v:v:v), and visualized by autoradiography. The PI([$^{32}$P]-3)P spots were then scraped off from the TLC plates, deacylated with 1 ml methylamine:butanol:methanol (42:9:47) (v:v:v) for 4 hours at 53° C., and quantitated using a liquid scintillation counter (LKB 1209 RackBETA).

The inhibitory concentration (µM) for each of the tested compounds is listed in Table IV below.

TABLE IV

| Compound | IC$_{50}$ (µM) |
| --- | --- |
| TGX-25 | ~11.1 |
| TGX-37 | ~10.5 |
| TGX-40 | ~1.5 |
| TGX-41 | ~9.8 |
| TGX-57 | 2 |
| TGX-84 | 0.1 |
| TGX-90 | 0.1 |
| TGX-93 | 1 |
| TGX-98 | 1 |
| TGX-99 | 1 |
| TGX-101 | 0.1 |
| TGX-102 | 0.1 |
| TGX-106 | 2 |
| TGX-107 | 1.0 |
| TGX-108 | 1 |
| TGX-109 | 1 |
| TGX-111 | 0.05 |
| TGX-112 | 0.5 |
| TGX-113 | 0.5 |
| TGX-115 | 0.05 |
| TGX-118 | 10.0 |
| TGX-120 | 1.0 |
| TGX-121 | 0.05 |
| TGX-123 | 0.2 |
| TGX-124 | 1.0 |
| TGX-125 | 25 |
| TGX-126 | 0.05 |
| TGX-127 | 0.05 |
| TGX-130 | 0.2 |
| TGX-131 | 0.5 |
| TGX-132 | 1.0 |
| TGX-133 | 5.0 |
| TGX-134 | 0.1 |
| TGX-135 | 0.2 |
| TGX-137 | 0.05 |
| TGX-138 | 1.0 |
| TGX-139 | 1.0 |
| TGX-140 | 10.0 |
| TGX-141 | 1.0 |
| TGX-142 | 2.0 |
| TGX-143 | 0.15 |
| TGX-144 | 2.0 |
| TGX-145 | 2.0 |
| TGX-146 | 0.5 |
| TGX-147 | 5.0 |
| TGX-148 | 10.0 |
| TGX-149 | 0.5 |
| TGX-151 | 0.5 |
| TGX-152 | 0.5 |
| TGX-153 | 20.0 |
| TGX-154 | 10.0 |
| TGX-155 | 0.02 |
| TGX-156 | 5.0 |
| TGX-157 | 5.0 |
| TGX-158 | 5.0 |
| TGX-159 | 10.0 |
| TGX-160 | 2.0 |
| TGX-161 | 0.5 |
| TGX-162 | 2.0 |
| TGX-163 | 1.0 |
| TGX-165 | 1.0 |
| TGX-167 | 0.05 |
| TGX-168 | 0.75 |
| TGX-169 | 7.5 |
| TGX-170 | 0.2 |
| TGX-173 | 0.1 |
| TGX-174 | 0.1 |
| TGX-176 | 0.5 |
| TGX-179 | 10.0 |
| TGX-180 | 1.0 |
| TGX-186 | 0.01 |

EXAMPLE 6

Flow-Based Reconstitution Assay

The effect of TGX-40 on platelet adhesion was examined using a flow-based adhesion assay. Washed platelets were pretreated with 10, 25, or 50 μM TGX-40, or control buffer (0.1% DMSO) for 30 minutes at 37° C. prior to reconstitution with red blood cells to a hematocrit of 50%. The platelets and reconstituted red blood cells were perfused through vWf-coated glass microslides for 1 minute at a shear rate of 1800 $s^{-1}$. Non-adherent cells were removed by washing for 10 minutes at 1800 $s^{-1}$ and the number of adherent platelet were quantitated and expressed as the mean±SEM. As illustrated graphically in FIG. 1, TGX40 inhibited the ability of platelets to adhere in a dose-dependent manner, showing a decrease of 51, 67 and 86% in platelet adhesion when platelets were pretreated with 10, 25, and 50 μM TGX-40.

EXAMPLE 7

Whole-Blood Flow Assay

Figure 2:
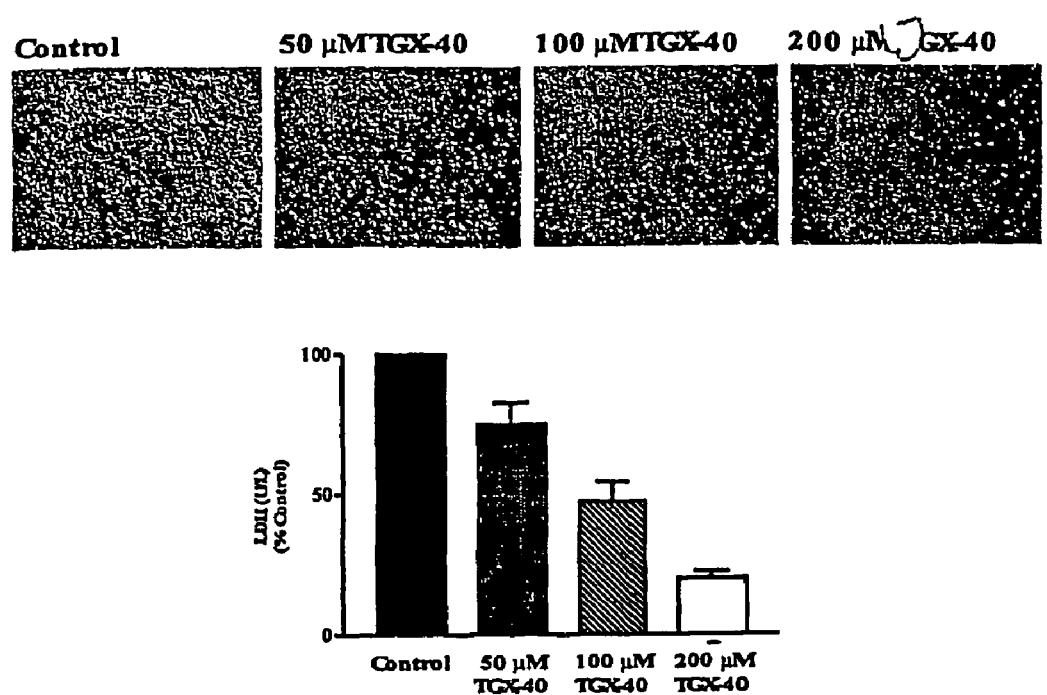
FIG. 2 shows photographs and a bar graph illustrating the effect, in a whole-blood flow assay, of various concentrations of TGX40 on the adhesion of platelets to vWf-coated glass microslides.

The inhibitory effect of TGX-40 on platelet thrombus formation was examined using a whole-blood flow assay, since thrombi formed by washed platelets are small and poorly reproducible. Anticoagulated whole blood was incubated with 50, 100, or 200 μM TGX-40, or control buffer (0.1% DMSO) for 30 minutes with gentle rocking prior to perfusion through vWf-coated glass microslides for 2 minutes at a shear rate of 1800 $s^{-1}$. Non-adherent platelets were removed by washing for 10 minutes at 1800 $s^{-1}$, and adherent erythrocytes were lysed with 1% ammonium oxalate. The level of thrombus formation was quantitated indirectly by measuring platelet LDH (U/L) levels in the whole cell lysates by spectrophotometry. Following a 2-minute perfusion of whole blood, platelet-rich thrombi were observed over the surface of the microslide. As seen in the photographs of FIG. 2, pretreatment with TGX-40 inhibited the ability of platelet thrombi to form on the vWf matrix in a dose-dependent manner. As illustrated graphically in FIG. 2, pretreatment of whole blood with 50, 100, and 200 μM TGX-40 led to a decrease of 25, 53, and 80% in thrombus formation relative to control.

EXAMPLE 8

Animal Model of Internal Carotid Artery Occlusion

The inhibitory effect of TGX-40 was examined in the well established animal model of arterial thrombosis of Folts et al., 1982, Circulation 65:248-255. This model is used to investigate the effects of antithrombotic drugs on clotting time in vivo in response to a crush injury followed by arterial stenosis.

The carotid artery of an anesthetized rat is dissected out, and an electromagnetic flow probe is placed around the artery to measure blood flow. Proximal to the flow probe, the artery is clamped with surgical forceps covered with silicone tubing to cause intimal and medial damage to the vessel wall. A ligature, or plastic cylinder of appropriate inside diameter is laced around the artery to produce a 70% reduction in arterial diameter.

Platelets aggregate in the area of the stenosed and damaged arterial vessel, gradually forming an occlusive platelet thrombus, seen as a decrease in blood flow. As the thrombus forms, blood pressure increases, causing the thrombus to fragment and embolize distal to the stenosed site. If the thrombus does not embolize spontaneously, the stenosed region is shaken gently to dislodge the thrombus. This causes a sudden restoration of blood flow. Platelets again aggregate in the area of the stenosed and damaged arterial vessel, repeating the thrombus-embolization pattern. This acute platelet-mediated thrombus formation, followed by embolization, causes Cyclic Flow Reductions (CFR) in blood flow. Once a rat produces regular CFRs, an anti-thrombotic compound or vehicle control is administered via the jugular vein.

Figure 3:
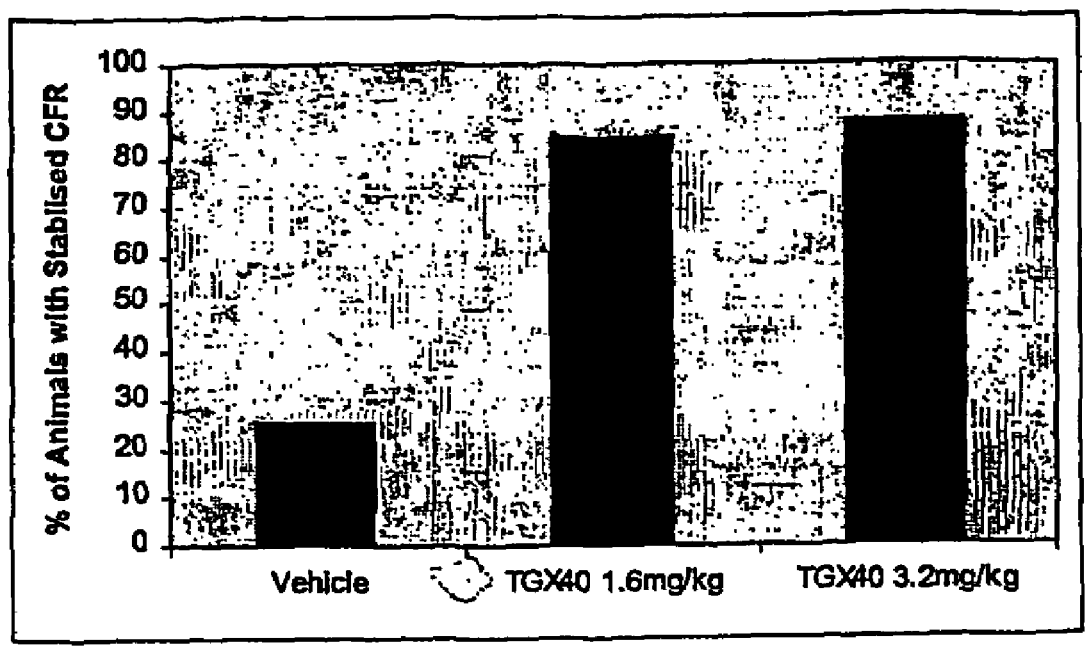
FIG. 3 shows a bar graph illustrating the effect, in an animal model of arterial occlusion, of two concentrations of TGX40 on the stabilization of blood flow in rats producing regular cyclic flow reductions (CFRs)

TGX-40 was administered at doses of 1.6 mg/kg and 3.2 mg/kg via the jugular vein and the stabilization of blood flow was recorded. As illustrated graphically in FIG. 3, TGX-40, at 1.6 mg/kg and 3.2 mg/kg, returned 90% of the treated animals to baseline within 10 minutes, indicating that the compound has utility in the treatment of coronary artery occlusion.

EXAMPLE 9

Effect of TGX84 on Platelet Thrombus Formation Under Flow

Figure 4:
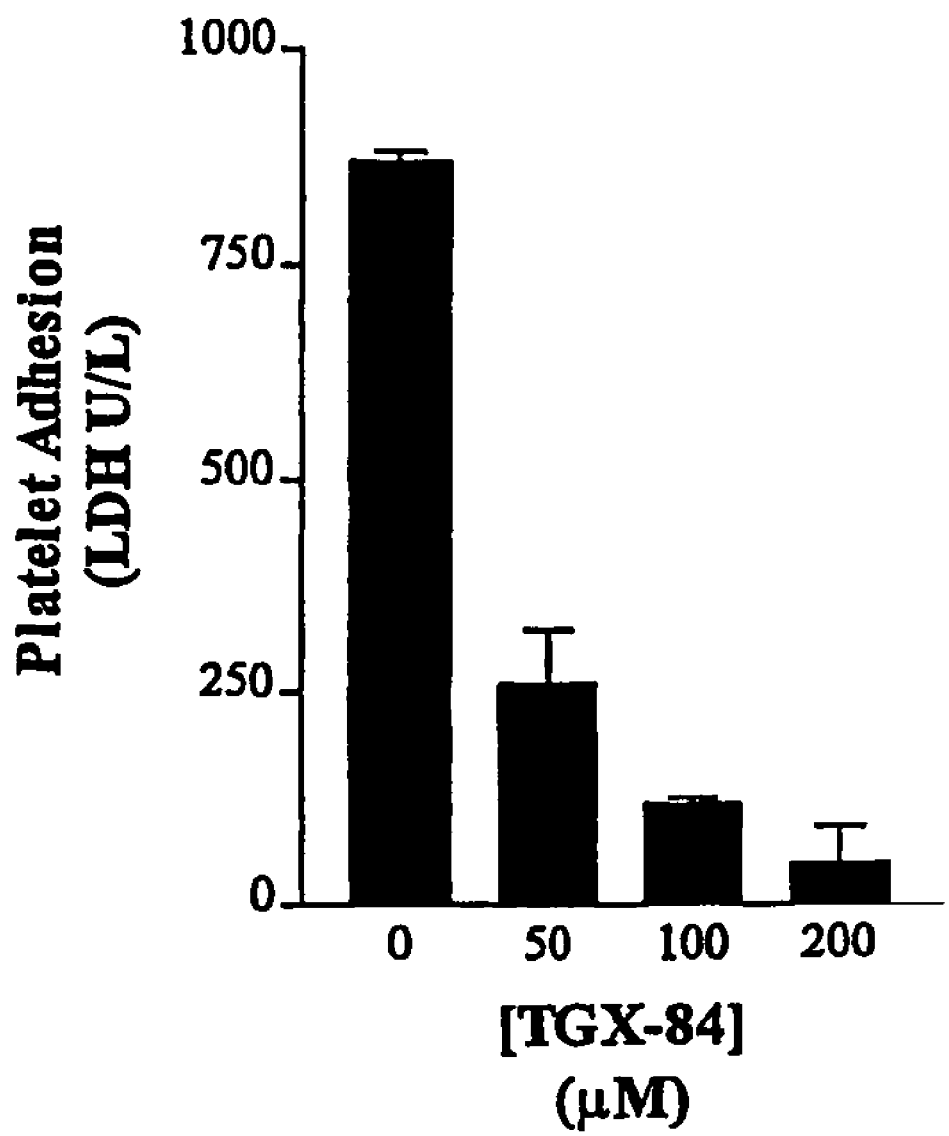
FIG. 4 shows a bar graph illustrating the effect, in a whole-blood flow assay, of various concentrations of TGX-84 on the platelet thrombus formation.

Citrated whole blood was pretreated with 50, 100 or 200 μM TGX-84, or control buffer (0.1% DMSO) for 10 minutes at 37° C. Blood was perfused through von Willebrand factor- (vWf) coated microcapillary tubes for 2 minutes at 600 $s^{-1}$. Non-adherent cells were removed by perfusion of buffer for 2 minutes at 600 $s^{-1}$ and any adherent erythrocytes lysed through treatment with 1% ammonium oxalate. Adherent platelets were then lysed through addition of 1% Triton X-100 and lactate dehydrogenase (LDH) levels (U/L) analysed by spectrophotometry. The results are graphically shown in FIG. 4. As illustrated in FIG. 4, pretreatment of whole blood with 50, 100, 200 μM TGX-84 led to a decrease in thrombosis formation relative to control.

EXAMPLE 10

In Vitro Enzyme Assays PI3K and PI4K

In vitro enzyme assays were conducted as a primary screen to determine drug candidate isoform affinity and specificity. The affinity of two leading compounds of the quinolone series (TGX84 and TGX155) for a closely related enzyme family, PI4K, was also determined to maximise compound specificity and therefore minimise potential adverse biochemical events.

The α and β isoforms of the PI3K were immunoprecipitated from a platelet lysate using an antibody that recognised the p85 regulatory subunit common to both forms of the enzyme. The γ isoform was produced as a recombinant protein in the Thrombogenix laboratories. PI4K was isolated from platelets in a similar manner using a PI4K specific antibody. Standard phosphorylation assays using phosphatidylinositol and $^{32}P$ were used to measure the enzyme activity in the immunoprecipates in the presence or absence of an inhibitor. Enzyme activity was determined over a range of inhibitor concentrations to establish an $IC_{50}$ value.

The $IC_{50}$ for LY294002 against the α/β isoforms of PI3K was in agreement with previously reported values (1-1.5 μM).

TABLE V

Affinity of LY294002 and Thrombogenix compounds for PI3K α/β isoforms

| Compound | Chemical class | PI3K α/β $IC_{50}$ (μM) | PI3K γ (μM) |
|---|---|---|---|
| LY294002 | — | 1-1.5 | 2 |
| TGX-155 | QU | 0.02 | 5 |
| TGX-127 | QU | 0.05 | 5-10 |
| TGX-115 | QU | 0.05 | 5 |
| TGX-167 | PP | 0.05 | 5-10 |
| TGX-137 | PP | 0.05 | 5 |
| TGX-126 | PP | 0.05 | >10 |
| TGX-183 | PP | 0.05 | |
| TGX-184 | BP | 0.05 | |
| TGX-121 | QU | 0.05 | 5 |
| TGX-111 | QU | 0.05 | >10 |
| TGX-84 | QU | 0.1 | 5 |
| TGX-101 | PP | 0.1 | 2 |
| TGX-174 | PP | 0.1 | 5 |
| TGX-134 | BP | 0.1 | 0.2 |
| TGX-102 | BP | 0.1 | 2 |
| TGX-90 | BP | 0.1 | 3 |
| TGX-143 | QU | 0.15 | 2 |
| TGX-173 | BP | 0.15 | |

QU - quinolone series;
PP - pyridopyrimidine series;
BP - benzopyranone series.

In contrast to its highly potent affinity for PI3K, TGX155 and TGX84 exhibited an $IC_{50}$ of 100 μM against PI4K.

EXAMPLE 11

Enzyme Screening Assay

The two leading compounds of the quinolone series, TGX155 and TGX84 were screened for activity against seven enzymes related to PI3K in function or substrate specificity, viz: ATPase, PDE4, tyrosine kinases EGF and fyn, protein kinases A and C, and tyrosine phosphatase. The $IC_{50}$ values for TGX155 and TGX84 inhibition of each enzyme were greater than 100 μM, confirming the target specificity of the compounds.

EXAMPLE 12

Cell Proliferation Assay

The anti-proliferative activity of the compounds of this invention from all three chemical classes was determined using K562 (leukaemia derived) and U937 (moncytic) cell lines. The cytotoxic activity of the compounds was monitored over four days by counting cell number and determining cell viability using a colourimetric assay metabolic activity.

Antiproliferative Activity of TGX Compounds (20 μM, 4 day incubation)

| Compound | % Cells remaining |
|---|---|
| TGX-168 | 15 |
| TGX-123 | 10 |
| TGX-167 | 1.5 |
| TGX-186 | 1.5 |
| TGX-40 | 75 |

These data demonstrate that the compounds are useful in preventing cell proliferation. Hence the compounds of this invention may be useful in the treatment of cancer and other disorders, such as asthma, where abnormal cell proliferation is involved.

EXAMPLE 13

Making and Administering Pharmaceutical Compositions that Contain Morpholino-Substituted Compounds Another aspect of the present invention relates to a pharmaceutical composition containing a morpholino-substituted compound of the present invention together with one or more pharmaceutically acceptable carriers and/or diluents. Below, the term "active ingredient" may be any morpholino-substituted compound of the present invention, or a physiologically acceptable salt, solvate, or functional derivative thereof.

Administration of this pharmaceutical composition is performed by any convenient means. Doses are administered daily, weekly, monthly, or at other suitable time intervals such as by the oral, intravenous, intraperitoneal, intramuscular, subcutaneous, intradermal, or suppository routes, or by implanting (e.g. using slow-release molecules). If the active compound is administered in tablet form, the tablet contains a binder such as tragacanth, corn starch, or gelatin; a disintegrating agent, such as alginic acid; and a lubricant, such as magnesium stearate.

The pharmaceutical compositions suitable for injectable use include sterile aqueous solutions or dispersions, and sterile powders for the extemporaneous preparation of sterile injectable solutions or dispersions, or are in the form of a cream or other form suitable for topical application. The carrier can be a solvent or dispersion medium containing, for example, water, ethanol, polyol (e.g., glycerol, propylene glycol, and liquid polyethylene glycol, and the like), suitable mixtures thereof, and vegetable oils. The proper fluidity is maintained, for example, by the use of a coating such as lecithin, by the maintenance of the required particle size in the case of dispersion, and by the use of superfactants. Prevention of contamination by microorganisms can be brought about by various antibacterial and antifungal agents, for example, parabens, chlorobutanol, phenol, sorbic acid, thimerosal and the like. It may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, followed by filter sterilization. Generally, dispersions are prepared by incorporating the various sterilized active compounds into a sterile vehicle containing the basic dispersion medium and one or more of the above-described ingredients. In the case of sterile powders for the preparation of sterile injectable solutions, the preferred methods of preparation are vacuum drying and freeze drying which yield a powder of the active compound plus any additional desired ingredients from previously sterile-filtered solutions thereof.

The pharmaceutical compositions are orally administered, for example, with an inert diluent or with an assimilable edible carrier, are enclosed in hard or soft shell gelatin capsule, are compressed into tablets, or are incorporated directly with food. For oral administration, the active compounds are incorporated with excipients, and are used in the form of ingestible tablets, buccal tablets, troches, capsules, elixirs, suspensions, syrups, wafers, and the like. Such compositions and preparations contain at least 1% by weight of active compound. The percentage of the compositions and preparations may be varied and may be between about 5 to about 80% of the weight of the unit. The amount of active compound in such therapeutically useful compositions is such that a suitable dosage will be obtained.

The tablets, troches, pills, capsules and the like may also contain a binder such as gum, acacia, corn starch, or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Some of the preferred pharmaceutical formulations of the present invention are described below.

Tablet Formulation for Oral Administration:

The ingredients of a tablet formulation for oral administration are listed in Table VI below. Tablets A, B, and C are prepared by wet granulation, with the povidone, of the first six ingredients listed in Table VI, followed by the addition of the magnesium stearate and subsequent compression.

TABLE VI

|  | Milligrams per Tablet | | |
| --- | --- | --- | --- |
|  | Tablet A | Tablet B | Tablet C |
| Active ingredient | 25 | 25 | 25 |
| Avicel | 13 | — | 7 |
| Lactose | 78 | 47 | — |
| Starch (maize) | — | 9 | — |
| Starch (pregelatinised, NF15) | — | — | 32 |
| Sodium starch glycollate | 5 | — | — |
| Povidone | 3 | 3 | — |
| Magnesium stearate | 1 | 1 | 1 |
| Total | 125 | 85 | 85 |

Tablet Formulation for Sublingual Administration:

The ingredients of two tablet formulations for sublingual administration are listed in Table 4 below. Tablets A and B are prepared by wet granulation, with the povidone, of the first six ingredients listed in Table 4, followed by the addition of the magnesium stearate and subsequent compression.

TABLE 4

|  | Milligrams per Tablet | |
| --- | --- | --- |
|  | Tablet A | Tablet B |
| Active ingredient | 25 | 25 |
| Avicel | 10 | — |

TABLE 4-continued

|  | Milligrams per Tablet | |
| --- | --- | --- |
|  | Tablet A | Tablet B |
| Lactose | — | 36 |
| Mannitol | 51 | 57 |
| Sucrose | — | 3 |
| Acacia | — | 3 |
| Povidone | 3 | — |
| Magnesium stearate | 1 | 1 |
| Total | 90 | 125 |

Tablet Formulation for Buccal Administration:

A tablet for buccal administration is prepared by admixing the ingredients listed in Table 5 below, followed by direct compression of the admixed ingredients.

TABLE 5

|  | Milligrams per Tablet |
| --- | --- |
| Active ingredient | 25 |
| Hydroxypropylmethyl cellulose (HPMC) | 25 |
| Polycarbophil | 39 |
| Magnesium stearate | 1 |
| Total | 90 |

Powder-Filled Capsule Formulation:

The ingredients of two powder-filled capsule formulations are listed in Table 6 below. Capsules A and B are prepared by admixing the ingredients, and filing two-part hard gelatin capsules with the resulting mixture.

TABLE 6

|  | Milligrams per Tablet | |
| --- | --- | --- |
|  | Capsule A | Capsule B |
| Active ingredient | 25 | — |
| Avicel | 45 | — |
| Lactose | 153 | — |
| Starch (1500 NF) | — | 117 |
| Sodium starch glycollate | — | 6 |
| Magnesium stearate | 2 | 2 |
| Total | 225 | 150 |

Liquid-Filled Capsule Formulation:

The ingredients of two liquid-filled capsule formulations are listed in Table 7 below. Capsule A is prepared by melting the Macrogol 4000 BP, dispersing the active ingredient in the melt, and filling two-part hard gelatin capsules therewith. Capsule B may be prepared by dispersing the active ingredient in the lecithin and arachis oil, and filling soft, elastic gelatin capsules with the resulting dispersion.

TABLE 7

|  | Milligrams per Tablet | |
| --- | --- | --- |
|  | Capsule A | Capsule B |
| Active ingredient | 25 | 25 |
| Macrogol 4000 USP | 200 | — |

TABLE 7-continued

|  | Milligrams per Tablet | |
| --- | --- | --- |
|  | Capsule A | Capsule B |
| Lecithin | — | 100 |
| Arachis oil | — | 100 |
| Total | 225 | 225 |

Controlled-Release Capsule Formulation:

A capsule formulation for controlled release is prepared by mixing and extruding the first four ingredients listed in Table 8 below, and spheronizing and drying the extrudate. The dried pellets are coated with the ethyl cellulose as a release-controlling membrane, and the resulting pellets are filled into two-part hard gelatin capsules.

TABLE 8

|  | Milligrams per Capsule |
| --- | --- |
| Active ingredient | 25 |
| Avicel | 123 |
| Lactose | 62 |
| Triethyl citrate | 3 |
| Ethyl cellulose | 12 |
| Total | 225 |

Intravenous Formulation:

The intravenous formulation containing the ingredients listed in Table 9 below is prepared by taking up the active ingredient in the citrate buffer, and the pH of the solution is then adjusted to pH 7 with hydrochloric acid. The resulting solution is made up to volume, and is subsequently filtered through a micropore filter into sterile glass vials which are sealed and oversealed after filling.

TABLE 9

|  | % by weight |
| --- | --- |
| Active ingredient | 2 |
| Hydrochloric acid (citrate buffer) | q.s. to pH 7 |
| Water for injections | to 100% |

Intranasal Formulation:

An intranasal formulation containing the ingredients listed in Table 10 below is prepared by taking up the active ingredient in a mixture of the hydroxybenzoates, and the pH of the solution is then adjusted to pH 7 with hydrochloric acid in citrate buffer. The resulting solution is made up to volume, and is subsequently filtered through a micropore filter into sterile glass vials which are sealed and oversealed after filling.

TABLE 10

|  | % by weight |
| --- | --- |
| Active ingredient | 0.5 |
| Hydrochloric acid in citrate buffer | q.s. to pH 7 |
| Methyl hydroxybenzoate | 0.2 |
| Propyl hydroxybenzoate | 0.2 |
| Water for injections | to 100% |

Intramuscular-Injection Formulation:

A formulation for intramuscular injection containing the ingredients listed in Table 11 below is prepared by dissolving the active ingredient in the glycofurol. The benzyl alcohol is then added and dissolved, and water is added to bring the final volume to 3 ml. The mixture is then filtered through a micropore filter into sterile glass vials which are sealed and oversealed after filling.

TABLE 11

| Active ingredient | 0.05 g |
| --- | --- |
| Benzyl alcohol | 0.1 g |
| Glycofuro 751 | 1.45 g |
| Water for injections | q.s. to 3.00 ml |

Syrup Formulation:

A syrup formulation containing the ingredients listed in Table 12 below is prepared by dissolving the sodium benzoate in a portion of purified water, and the sorbitol solution is then added. Subsequently, the active ingredient is added and dissolved. The resulting solution is then mixed with the glycerol and made up to the required volume with purified water.

TABLE 12

| Active Ingredient | 0.05 g |
| --- | --- |
| Sorbitol solution | 1.5 g |
| Glycerol | 1.0 g |
| Sodium benzoate | 0.005 g |
| Flavor | 0.0125 ml |

Suppository Formulation:

A suppository formulation containing the ingredients listed in Table 13 below is prepared by melting one-fifth of the Witepsol in a steam-jacketed pan at a maximum temperature of 45° C. The active ingredient is then sifted through a 200 μm sieve and mixed with the molten base using a Silverson mixer fitted with a cutting head until a smooth dispersion is achieved. Maintaining the mixture at 45° C., the remaining Witepsol H15 is added to the suspension which is stirred to ensure a homogenous mix. The entire suspension is then passed through a 250 μm stainless steel screen and, with continuous stirring, allowed to cool to 40° C. At a temperature of between 38 and 40° C., 2.0 g aliquots of the mixture are filled into suitable plastic molds. The resulting suppositories are allowed to cool to room temperature.

TABLE 13

|  | Milligrams per Suppository |
| --- | --- |
| Active ingredient (63 μm)[1] | 50 |
| Hard fat, USP (Witepsol H15 - dynamit NoBel) | 1950 |
| Total | 2000 |

[1]The active ingredient is used as a powder wherein at least 90% of the particles are of 63 μm diameter or less.

Aerosol Formulation:

An aerosol formulation containing the ingredients listed in Table 14 below is prepared by mixing the active compound with ethanol, and water is added for injection. The solution is subsequently added to a portion of the Propellant 22, cooled to −30° C., and transferred to a filling device. The required amount is then fed to a stainless steel container and diluted with the remainder of the propellant. The valve units are then fitted to the container.

TABLE 14

|  | % by weight |
| --- | --- |
| Active ingredient | 0.25 |
| Ethanol | 10 |
| Water for injections | 19.75 |
| Propellant 22 (chlorodifluoromethane) | 70 |
| Total | 100 |

Pessary Formulation:

A pessary formulation is prepared by directly mixing the ingredients listed in the Table 15 below. Pessaries are prepared by compressing the resulting mixture.

TABLE 15

|  | Milligrams per Pessary |
| --- | --- |
| Active ingredient (63 μm)[1] | 50 |
| Anhydrous dextrose | 470 |
| Potato starch | 473 |
| Magnesium stearate | 473 |
| Water for injections | 1000 |

[1]The active ingredient is used as a powder wherein at least 90% of the particles are of 63 μm diameter or less.

What is claimed is:

1. A compound having the following formula (II):

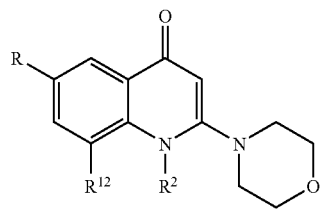

(II)

wherein

R and $R^2$ are independently H, OH, F, Cl, Br, I, $C_1$-$C_6$ alkyl, aryl or $(CH_2)_n$-aryl;

$R^{12}$ is $C_3$-$C_6$ cycloalkyl, CH=CH-aryl, C≡C-aryl, $(CHR^3)_n$-aryl, $NR^3$-cycloalkyl, $NR^3$—$(CHR^3)_n$-aryl, $(CHR^3)_n$—$NR^3$-aryl, $(CHR^3)_n$—$NR^3$-cycloalkyl, $(CHR^3)_n$—O-aryl, $(CHR^3)_n$—O-cycloalkyl, O—$(CHR^3)_n$-aryl, S—$(CHR^3)_n$-aryl, 4-methylbenzensulfonate, or CO-aryl, wherein n is 0, 1, or 2 and alkyl, cycloalkyl or aryl is optionally substituted with F, Cl, Br, I, CN, $CO_2H$, $CO_2R^3$, $NO_2$, $CF_3$, substituted or unsubstituted $C_1$-$C_6$ alkyl, substituted or unsubstituted cycloalkyl, substituted or unsubstituted aryl, $OCF_3$, $OR^3$, $OSO_2$-aryl, substituted or unsubstituted amine, $NHCOR^3$, $NHSO_2R^3$, $CONHR^3$, or $SO_2NHR^3$; and $R^3$ is H, or substituted or unsubstituted $C_1$-$C_6$ alkyl, substituted or unsubstituted aryl.

2. The compound (II) of claim 1, wherein $R^{12}$ is selected from a group consisting of

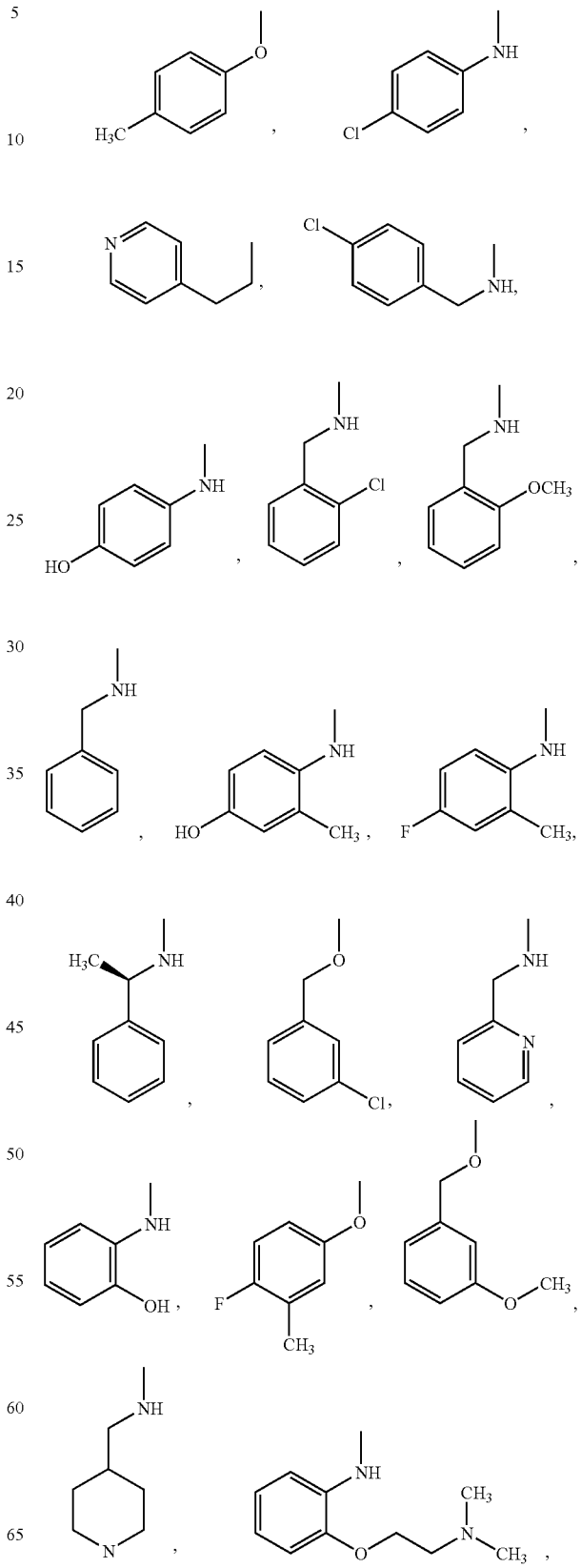

-continued

3. The compound (II) of claim 1, wherein R is H, $R^{12}$ is phenoxy and $R^2$ is H.

4. The compound (II) of claim 1, wherein R is H, $R^{12}$ is 2-methylphenoxy and $R^2$ is H.

5. The compound (II) of claim 1, wherein R is H, $R^{12}$ is 2-methyl-4-fluorophenoxy and $R^2$ is H.

6. A method for treating cardiovascular disease in a patient, comprising administering to the patient a therapeutically effective amount of the compound of claim, wherein said cardiovascular disease is coronary artery occlusion, stroke, acute coronary syndrome, acute myocardial infraction, restenosis, atherosclerosis, or unstable angina.

7. The method of claim 6, wherein the compound is in the form of a dose.

8. The method of claim 7, wherein the dose is in the form of a tablet, capsule, intravenous formulation, intranasal formulation, transdermal formulation, formulation for muscular injection, syrup, suppository, aerosol, or pessary.

9. The method of claim 8, wherein the tablet is formulated for oral, sublingual, or buccal administration.

10. The method of claim 7, wherein the dose contains from about 5 to about 500 mg of the compound.

11. The method of claim 10, wherein the dose contains from about 25 to about 300 mg of the compound.

12. A method for treating respiratory disease in a patient, comprising administering to the patient a therapeutically effective amount of the compound of claim 1, wherein said respiratory disease is asthma, chronic obstructive pulmonary disease or bronchitis.

13. The method of claim 12, wherein the compound is in the form of a dose.

14. The method of claim 13, wherein the dose is in the form of a tablet, capsule, intravenous formulation, intranasal formulation, transdermal formulation, formulation for muscular injection, syrup, suppository, aerosol, or pessary.

15. The method of claim 14, wherein the tablet is formulated for oral, sublingual, or buccal administration.

16. The method of claim 13, wherein the dose contains from about 5 to about 500 mg of the compound.

17. The method of claim 16, wherein the dose contains from about 25 to about 300 mg of the compound.

18. A compound having the following formula:

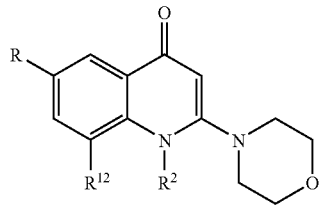

wherein
R and $R^2$ are independently H, OH, F, Cl, Br, I, $C_1$-$C_6$ alkyl, aryl or $(CH_2)_n$-aryl; and
$R^{12}$ is OH, F, Cl, Br, I or CHO.

19. A compound selected from the group consisting of:
8-(4-fluoro-2-methylphenoxy)-2-morpholinoquinolin-4(1H)-one (TGX 155)
8-(m-tolyloxy)-2-morpholinoquinolin-4(1H)-one (TGX 127)
8-(o-tolyloxy)-2-morpholinoquinolin-4(1H)-one (TGX 115)
8-(4-fluorophenoxy)-2-morpholinoquinolin-4(1H)-one (TGX 121)
2-morpholino-8-(phenylthio)quinolin-4(1H)-one (TGX 111)
2-morpholino-8-phenoxyquinolin-4(1H)-one (TGX 084)
8-(4-chloro-2-methylphenoxy)-2-morpholinoquinolin-4(1H)-one (TGX 180)
8-(2-fluorophenoxy)-2-morpholinoquinolin-4(1H)-one (TGX 143)
8-(p-tolyloxy)-2-morpholinoquinolin-4(1H)-one (TGX 113)
methyl 3-(1,4-dihydro-2-morpholino-4-oxoquinolin-8-yloxy)benzoate (TGX 149)
sodium 3-(1,4-dihydro-2-morpholino-4-oxoquinolin-8-yloxy)benzoate (TGX 152)
3-(1,4-dihydro-2-morpholino-4-oxoquinolin-8-yloxy)benzoic acid (TGX 151)
1-methyl-2-morpholino-8-phenoxyquinolin-4(1H)-one (TGX 171)
8-(4-fluorobenzyl)-2-morpholinoquinolin-4(1H)-one (TGX 099)
8-(4-methylbenzyl)-2-morpholinoquinolin-4(1H)-one (TGX 106)
8-benzyl-2-morpholinoquinolin-4(1H)-one (TGX 057)
2-morpholino-8-phenylquinolin-4(1H)-one (TGX 070)
1-methyl-2-morpholino-8-phenylquinolin-4(1H)-one (TGX 071)
8-acetylphenyl-2-morpholinoquinolin-4(1H)-one (TGX 086)
8-benzyl-1-methyl-2-morpholinoquinolin-4(1H)-one (TGX 074) and
1,4-dihydro-1-methyl-2-morpholino-4-oxoquinolin-8-yl 4-methylbenzenesulfonate (TGX 138).

* * * * *